US010060898B2

(12) United States Patent
Gupta

(10) Patent No.: US 10,060,898 B2
(45) Date of Patent: Aug. 28, 2018

(54) EXPANDABLE JACKET FOR TRIAXIAL, UNCONFINED AND UNIAXIAL COMPRESSION TESTS AND TEST DEVICE FOR THREE-DIMENSIONAL CONSOLIDATION AND SETTLEMENT TESTS

(71) Applicant: Ramesh Chandra Gupta, Ashburn, VA (US)

(72) Inventor: Ramesh Chandra Gupta, Ashburn, VA (US)

( * ) Notice: Subject to any disclaimer, the term of this patent is extended or adjusted under 35 U.S.C. 154(b) by 0 days.

(21) Appl. No.: 15/838,660

(22) Filed: Dec. 12, 2017

(65) Prior Publication Data

US 2018/0120283 A1    May 3, 2018

Related U.S. Application Data

(63) Continuation-in-part of application No. 15/452,267, filed on Mar. 7, 2017, now Pat. No. 9,880,081.

(51) Int. Cl.
*G01N 19/06* (2006.01)
*G01N 33/24* (2006.01)
(Continued)

(52) U.S. Cl.
CPC ............. *G01N 33/24* (2013.01); *E02D 1/025* (2013.01); *E02D 1/027* (2013.01); *G01N 3/08* (2013.01)

(58) Field of Classification Search
None
See application file for complete search history.

(56) References Cited

U.S. PATENT DOCUMENTS 9,383,346 B2   7/2016  Gupta
9,546,940 B2   1/2017  Gupta
(Continued)

FOREIGN PATENT DOCUMENTS

WO   WO2016/196734 A   8/2016
WO   WO2016/149128 A   9/2016

OTHER PUBLICATIONS

ASTM Standards, Standard Test Methods for Unconsolidated-Undrained Triaxial Compression Tests on Cohesive Soils. ASTM D2850-03, American Society for Testing and Materials,2007, Philadelphia, PA.
(Continued)

*Primary Examiner* — Andre Allen

(57) ABSTRACT

The expandable jacket and flexible ring comprises of the segmented circular arch shaped plates and bands or rings around the segmented plates. The test preparation consists of a membrane surrounding a specimen with or without a filter, segmented plates surrounding the membrane, and bands or rings around the segmented plates to permit uniform radial expansion of the specimen through its height when increments of vertical load are applied during the test, thereby providing accurate values of area of cross-section, deviator stress, volume change, modulus of elasticity, Poisson's ratio and shear strength. Using the flexible ring, three-dimensional consolidation tests are performed to determine three-dimensional coefficient of consolidation and coefficients of consolidation in horizontal and vertical directions. Removable attachments are used for assembling the expandable jacket and flexible ring during the test. A calibration device is used to determine the modulus of elasticity of the membrane and expandable jacket and flexible ring.

18 Claims, 16 Drawing Sheets

(51) Int. Cl.
E02D 1/02 (2006.01)
G01N 3/08 (2006.01)

(56) References Cited

U.S. PATENT DOCUMENTS

| | | |
|---|---|---|
| 9,567,722 B2 | 2/2017 | Gupta |
| 2015/0267370 A1 | 9/2015 | Gupta |
| 2015/0268217 A1 | 9/2015 | Gupta |
| 2016/0356685 A1 | 12/2016 | Gupta |

OTHER PUBLICATIONS

ASTM Standards, Standard Test Methods for Consolidated-Undrained Triaxial Compression Tests on Cohesive Soils. ASTM D4767-11, American Society for Testing and Materials, 2011, Philadelphia, PA.
AASHTO, Standard Method of Test for One-Dimensional Consolidation Properties of Soils, American Association of State Highway and Transportation Officials, 2012, Washington, D.C.
ASTM Standards, Standard Test Method for Determining One-Dimensional Consolidation Properties of Solis, ASTM D2435/ D2435 M, American Society for Testing and Materials, 2011, Philadelphia, PA.
ASTM Standards, Standard Test Method for Compressive Strength and Elastic Moduli of Rocks. ASTM: D 7012. American Society for Testing and Materials, 2011, Philadelphia, PA.
Bishop, A. W. and Green, G. E., "The influence of end restraint on the compression strength of a cohesionless soil," Geotechnique, 1965, pp. 243-266, vol. 15, London, UK.
Fang, H. Foundation Engineering Handbook, 2nd Edition, 1990, Van Nostrand Reinhold, New York, NY.
Lee, K. L., "End restraint effects on undrained static triaxial strength of sand," Journal of Geotechnical Engineering Division, 1978, pp. 687-703, vol. 104, New York, NY.
Perloff, W. H., and Baron, W., Soil Mechanics, John Wiley and Sons, 1976, New York, NY.
Rochelle, P. L., Leroueil, S., Trak, B., Blais-Lerox, L., and Tavenas, F., "Observational approach to membrane and area corrections in triaxial tests," Advanced Triaxial Testing of Soil and Rock, ASTM, STP 977, Eds. R. T. Donaghe, Chaney, R. C., Silver, M. L., ASTM, 1988, pp. 715-731, Philadelphia, PA.
Rowe, P. W. and Barden, L., "Importance of free ends in biaxial testing," Journal of Soil Mechanics and Foundations Division, ASCE, 1964, pp. 1-27, vol. 90, No. SM1, New York, NY.
Skempton, A. W., and Bjerrum, L., A Contribution to the Settlement Analyses of Foundations on Clay, Geotechnique, 1957, vol. 7, No. 3, London, UK.
Winterkorn, H. F., and Fang, H., Foundation Engineering Handbook, Van Nostrand Reinhold Company, 1975, New York, NY.
ASTM Standards, Standard Test Method for Determining One-Dimensional Consolidation Properties of Soils, ASTM D2435/ D2435 M, American Society for Testing and Materials, 2011, Philadelphia, PA.
Fang, H, Foundation Engineering Handbook, 2nd Edition, 1990, Van Nostrand Reinhold, New York, NY.
Rowe, P. W. and Barden, L., "Importance of free ends in triaxial testing," Journal of Soil Mechanics and Foundations Division, ASCE, 1964, pp. 1-27, vol. 90, No. SM1, New York, NY.

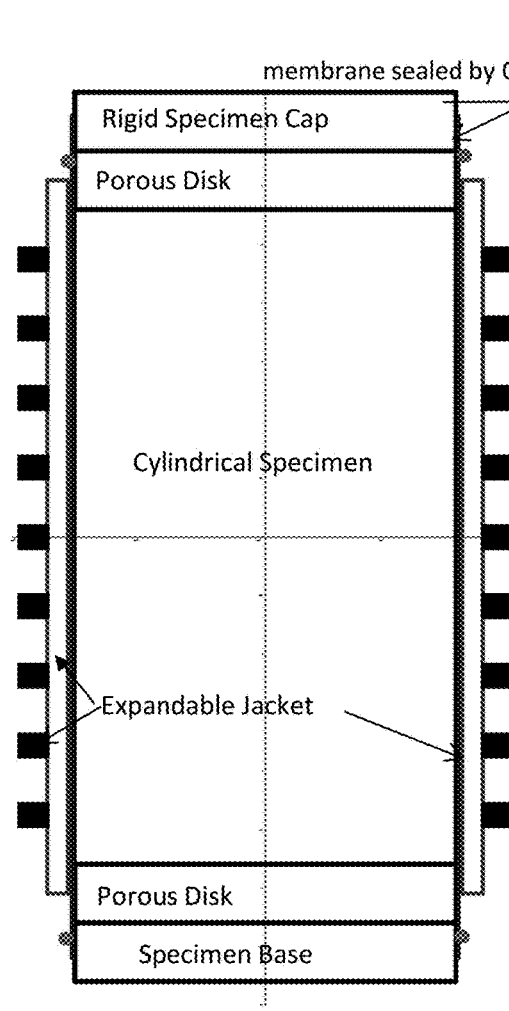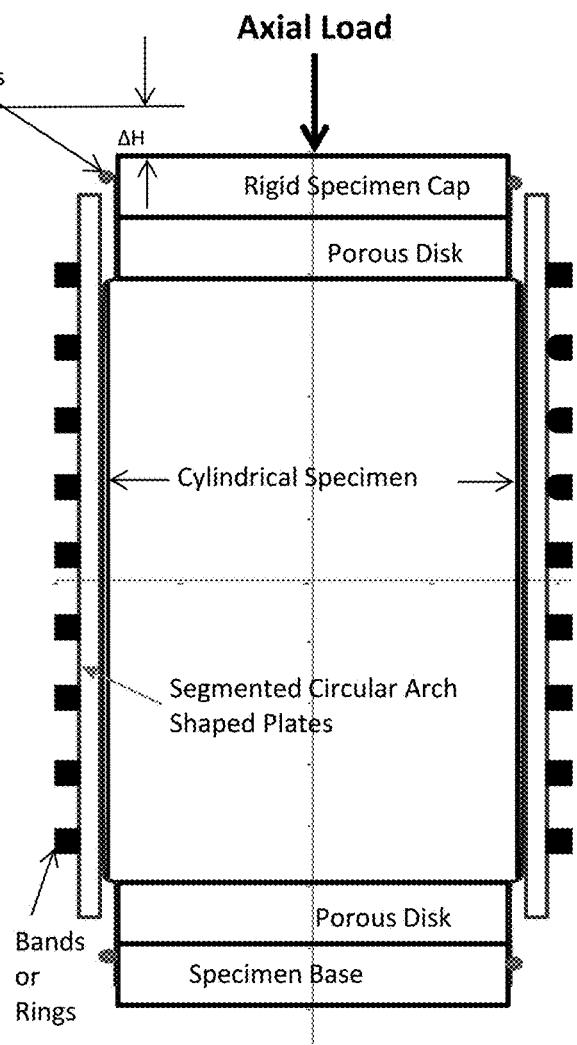
FIG. 2A
FIG. 2B

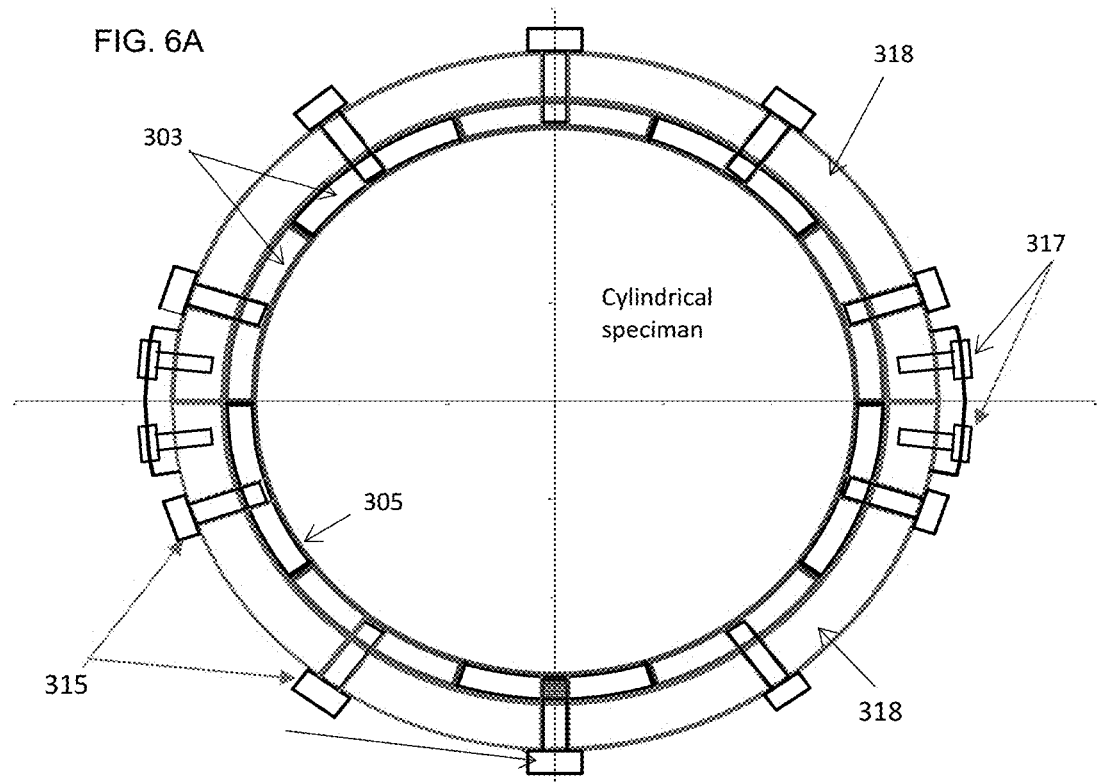
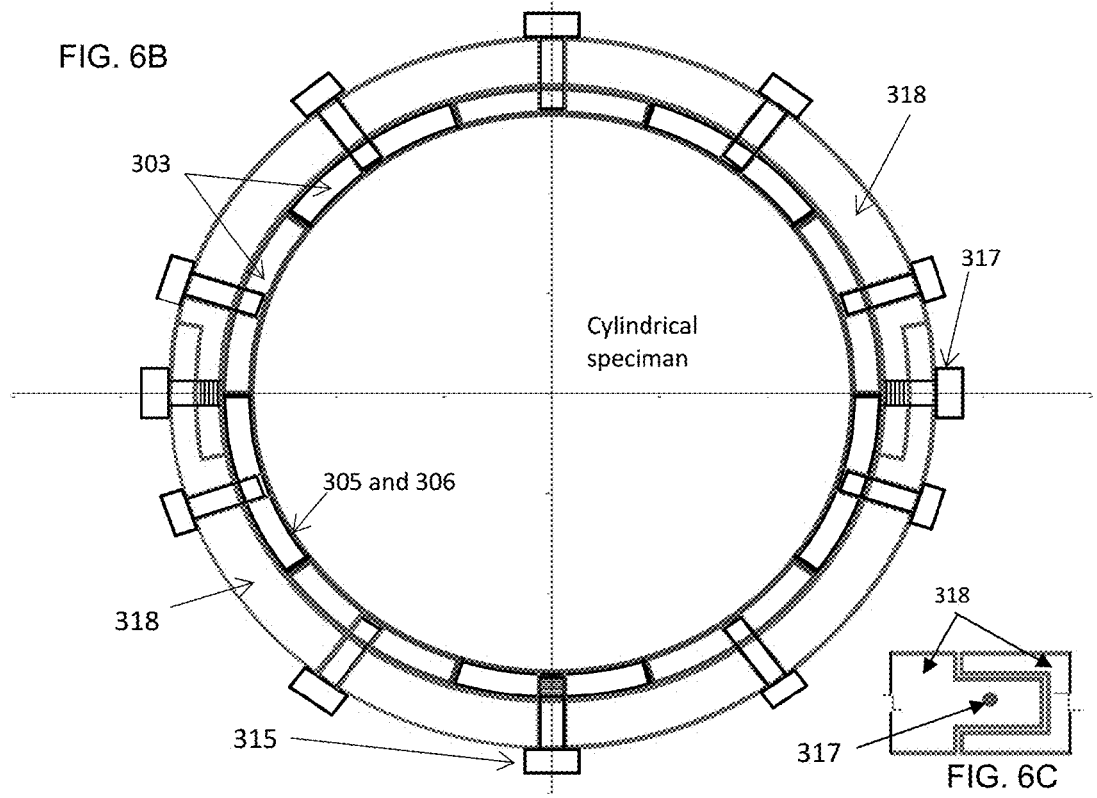

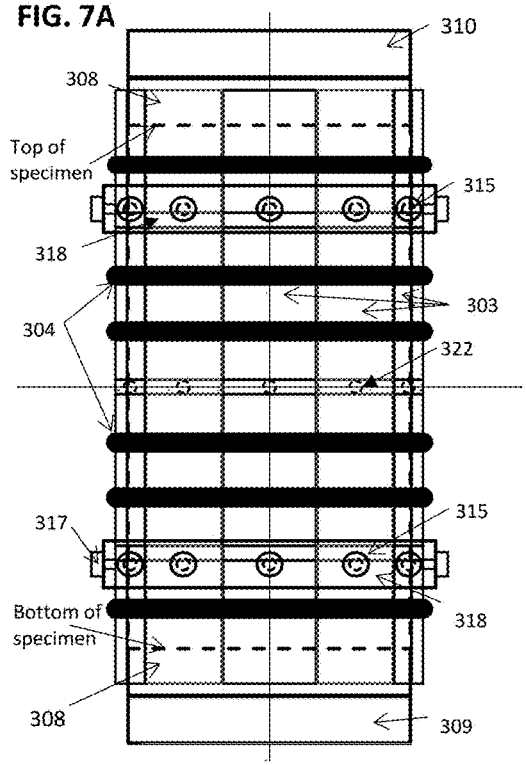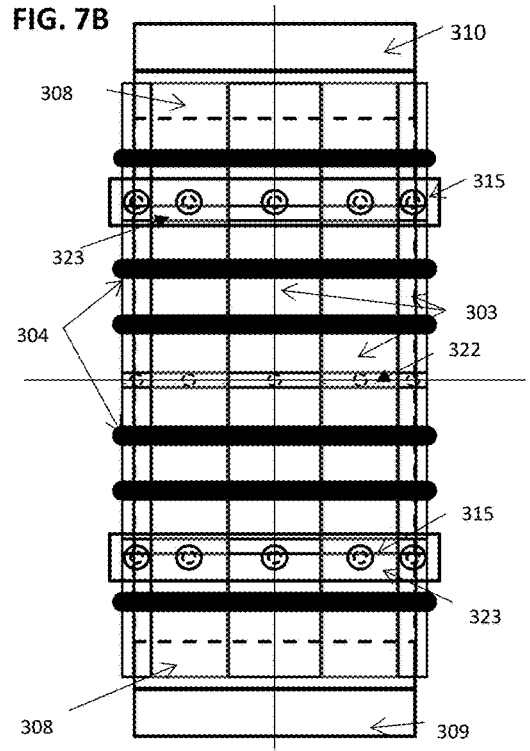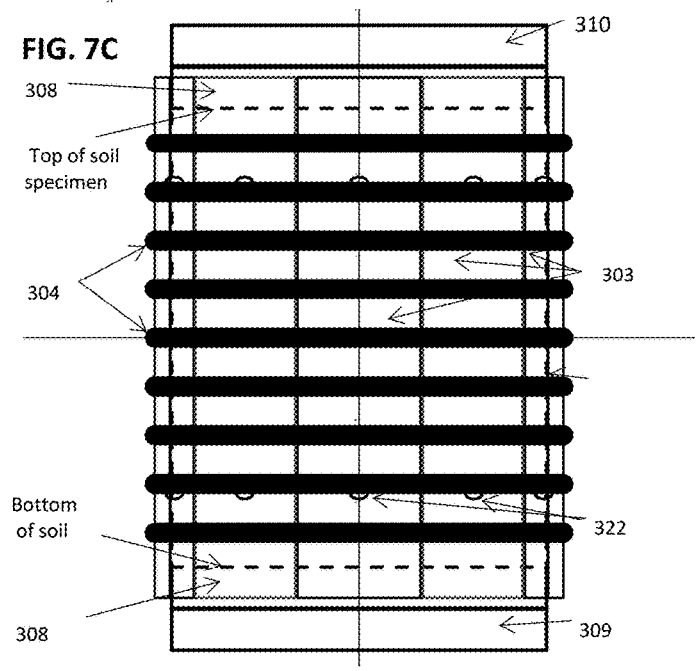

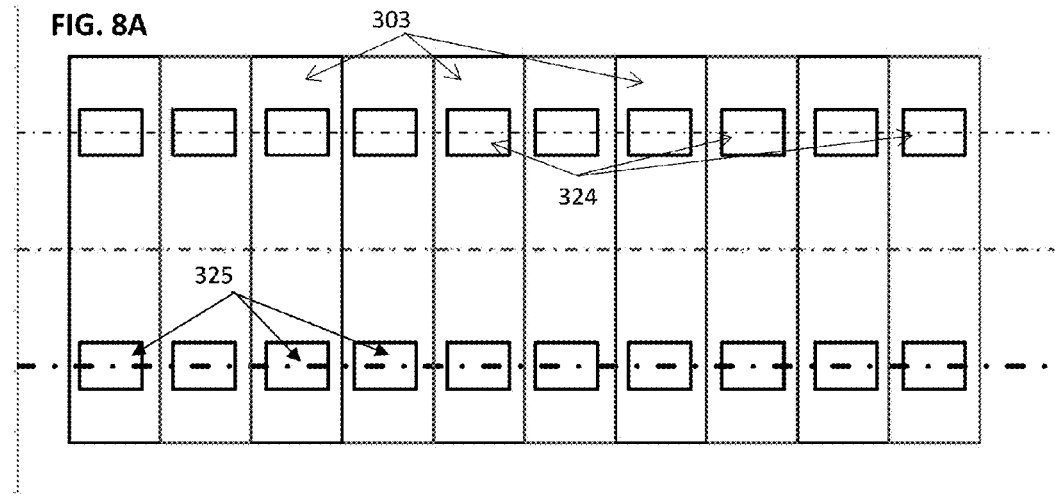
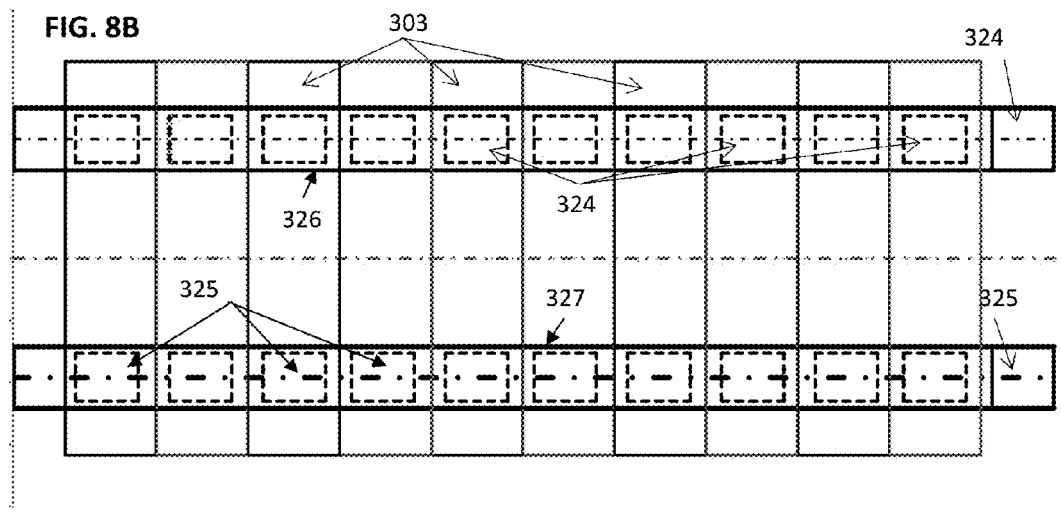
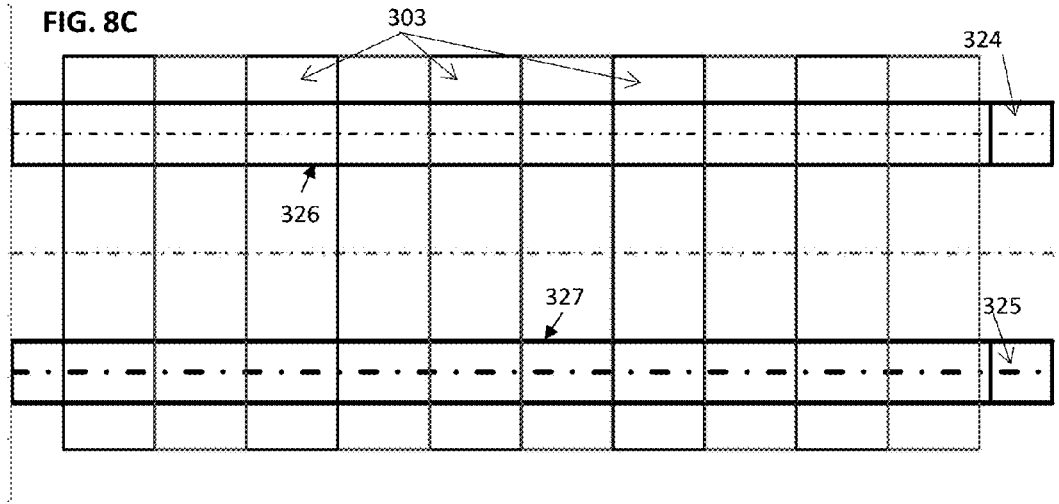

FIG. 14A

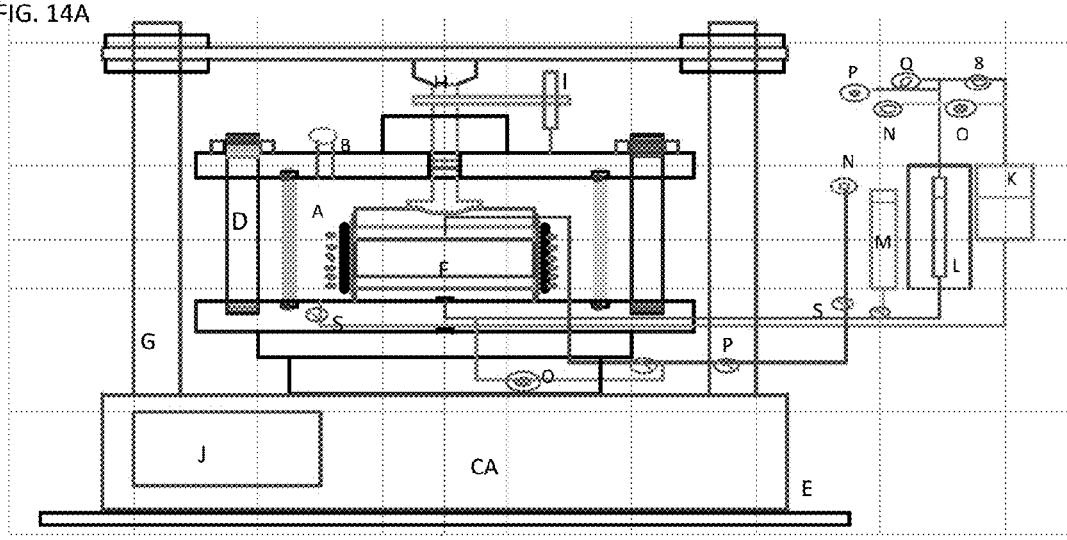

FIG. 14B

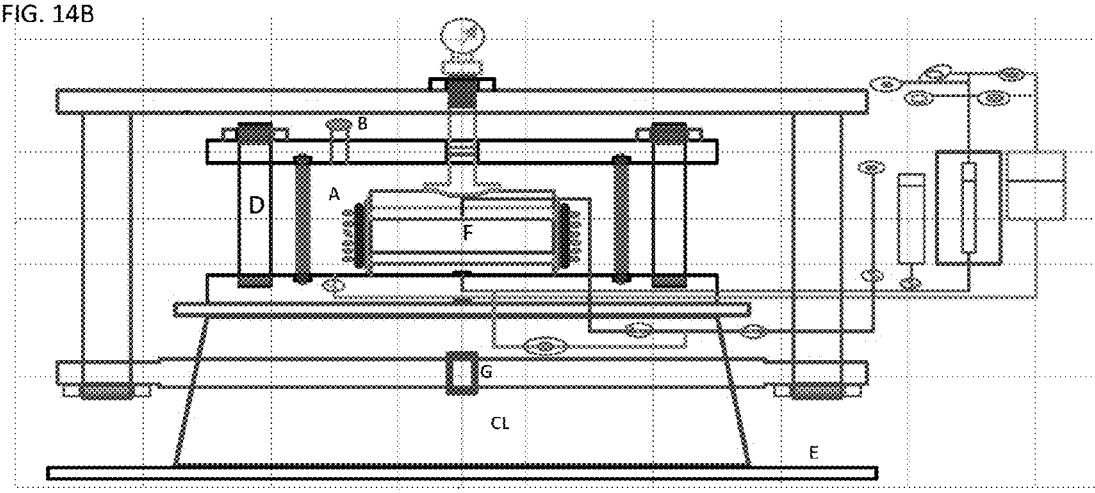

LEGEND

For Chamber and Loading Device
A  Acrylic Chamber/Cell
B  Vent
CA  Axial Loading Device, CL Incremental Loading Device
D  Clamping Rods for Chamber
E  Table Top
F  3-D Consolidation Test Sample Assembly
G  Loading Frame with Rods
H  Load Cell (or Prooving Ring)
I  Deformation Transducer (or Dial Gage)
J  Regulator Board for Strain Rates

For Control Panel
K  Chamber Pressure Reservoir
L  Volume Change Burette
M  Water Reservoir
N  Vacuum Regulator
O  Differential Pressure Transducer
P  Back Pressure Transducer
Q  Back Pressure Regulator
R  Cell Pressure Regulator (Differential)
S  Valves

EXPANDABLE JACKET FOR TRIAXIAL, UNCONFINED AND UNIAXIAL COMPRESSION TESTS AND TEST DEVICE FOR THREE-DIMENSIONAL CONSOLIDATION AND SETTLEMENT TESTS

TECHNICAL FIELD

This application is for applying for a utility patent in the technical field including civil engineering and geotechnical engineering testing. This specification/description is complete-in-itself. This invention is not sponsored or supported by federally sponsored research or development. This invention has been developed by me, Dr. Ramesh Chandra Gupta, Ph. D., P. E, President and Sole Owner of SAR6 INC., solely at my own cost and time. There is no joint research agreement with anyone. As stated earlier, this research/invention was conceived and completed solely by me (Dr. Ramesh C. Gupta, the inventor). It is my individual research work for this invention. The inventor is a citizen of U.S.

BACKGROUND OF THE INVENTION

An expandable jacket for the specimen of a triaxial compression test, unconfined compression test and uniaxial compressive strength tests for soils, intermediate geomaterials, soft and jointed rocks, intact rock and concrete core have been invented with the primary objective of maintaining the uniform increase of the diameter of the specimen throughout its height during the test, without forming a barrel shape or local bulging of the specimen. Since $20^{th}$ century, the main criticism of these tests has been that the specimen forms a barrel shape sometimes with local bulging causing premature failure of the specimen and does not afford the accurate determination of the area of cross-section, deviator stress and shear strength.

In this invention, the expandable jacket for three-dimensional consolidation and settlement tests to determine consolidation and settlement properties of soils and intermediate geomaterials has been termed as a flexible ring. Presently, one-dimensional consolidation tests using fixed ring are performed to determine the consolidation properties in vertical direction since the $20^{th}$ century, even though it has been known since that time that the consolidation and settlement of soils under a loaded area always occurs in a vertical as well as horizontal (radial) directions, i.e. in all three dimensions. In view of this, a test device using the flexible ring for determining three-dimensional consolidation and settlement properties of soils and intermediate geomaterials has been invented in this application.

The expandable jacket and flexible ring have been primarily invented for allowing uniform radial expansion of the cylindrical specimen when an axial/vertical load is applied on it. The flexible ring and expandable jacket around the cylindrical specimen comprises the segmented circular arch shaped plates around the specimen and stretchable bands or rings around the plates. The flexible ring and expandable jacket are to be installed around a specimen (generally of cylindrical shape) to perform these tests. Test preparation includes (i) installing a stretchable and impermeable membrane surrounding the specimen or surrounding the filter which surrounds the specimen, and (ii) placing a filter disk between specimen and the bottom porous disk and a filter disk between specimen and top porous disk, after which the expandable jacket or flexible ring consisting of segmented plates and stretchable bands or rings is installed surrounding the membrane. Stretchable bands or rings around the segmented plates permit uniform radial expansion to maintain uniform diameter of the specimen and apply lateral pressure on the specimen during the test.

For saturated soils and intermediate geomaterials, radial expansion of the specimen can be calculated by (i) the pore-water expelled out of the specimen and measured in a burette of control panel or (ii) by other methods such as electronic measurements by a linear variable displacement transformer (LVDT) or strain gages, or (iii) by simply assuming a value of Poisson's ratio. For partially saturated or dry soils, radial expansion of the specimen can be determined by methods (ii) or (iii) as described in the preceding sentence. To prevent bending of the LVDT probe, the LVDT is removably attached to a spring-loaded U-frame or U-frame without springs, wherein the U-frame rests on ball bearings.

The expandable jacket and flexible ring can be installed using removable attachments. For calibration of expandable jacket and flexible ring and to determine modulus of elasticity of the membrane and combined modulus of elasticity of expandable jacket and flexible ring, a calibration device is used, which comprises of a vertically movable water reservoir and a horizontal porous tube connected to a movable water reservoir or a pressure chamber as described in here-in-after.

SUMMARY OF INVENTION

(a) Technical Problem

Triaxial compression tests, unconfined compression tests and uniaxial compression strength tests on rocks have been performed to design geotechnical structures and substructures. The criticism of triaxial test since 20th century has been that during the test, the cylindrical specimen forms a barrel shape sometimes with localized bulging, resulting in premature failure of the specimen, inaccurate determination of the area of cross-section, the deviator stress, shear strength, and modulus of elasticity and significantly affecting the accuracy of volume change characteristics. Unconfined compression tests on cohesive soils or uniaxial compression strength tests on soft rocks is primarily performed to determine the shear strength or compression strength, but the accuracy of its value becomes questionable due to above cited shortcomings such as due to the barrel shape and possible local bulging of the specimen.

From $20^{th}$ century, one-dimensional consolidation test using a fixed ring has been performed to determine consolidation characteristics only in vertical direction, even though it has been known since then that the consolidation of the soils under a loaded area is generally or always controlled by the dissipation of excess pore-water pressures both in horizontal (radial) directions and vertical direction, resulting in settlement both in horizontal (radial) and vertical directions. Therefore, the consolidation characteristics so far determined from one-dimension consolidation test does not correctly define the consolidation properties of soils, resulting in incorrect prediction of the consolidation and final settlement and of structural behavior of the civil engineering structurers.

(b) Solution to Problem

To solve the above cited problems, the expandable jacket 301 and flexible ring 302 have been invented to accurately determine primarily the properties of soils and intermediate geomaterials, as described above in the Background of the Invention.

(c) Advantageous Effects of Invention

The expandable jacket shall allow uniform radial expansion throughout the height of the cylindrical specimen resulting in determination of the area of cross-section, the deviator stress, shear strength, Poisson's ratio and modulus of elasticity and volume change characteristics, accurately. The flexible ring shall permit determination of all three components of three-dimensional consolidation properties, i.e., coefficient of consolidation in vertical direction, coefficient of consolidation in horizontal direction, and three-dimensional coefficient of consolidation. Having determined accurately the properties of soils, and intermediate geomaterials by use the device/devices invented in this invention, it shall be possible to provide safe and economic design of geotechnical structures, and predict their time rate of consolidation and settlement accurately.

BRIEF DESCRIPTION OF THE SEVERAL VIEWS OF THE DRAWINGS

FIG. 2A shows the expandable jacket around the specimen. FIG. 2B Shows that the expandable jacket maintains cylindrical shape because of uniform radial displacement through its height during the triaxial compression tests.

FIG. 6A and FIG. 6B describe the plan view of the segmented circular arch-shaped plates 303 assembled in position with the help of half-circular brackets 318. FIG. 6C shows two half circular shaped brackets 318 fastened by screw 317.

FIG. 7A describes the elevation of view of the segmented circular arch-shaped plates 303 assembled in position with the help of two half-brackets 318. FIG. 7B describes the elevation of view of the segmented circular-arch shaped plates 303 assembled in position with the help of hook and loop straps 323. FIG. 7C shows elevation view when the installation of the expandable jacket 301 is completed.

FIG. 8A shows small pieces of removable adhesive loop or hook (324 or 325) strap placed on each segmented plate 303. FIG. 8B shows installing a hook and loop straps 326 or 327 on the pieces of adhesive loop straps (324 or 325) to assemble segmented plates 303 in proper configuration. FIG. 8C shows removable adhesive hook and loop strap placed directly on the segmented plates.

FIG. 14A shows the triaxial type chamber, triaxial type loading frame, axial loading device, triaxial type chamber control panel and the flexible ring 302 containing cylindrical specimen of soils or intermediate geomaterials or soft rock. FIG. 14B shows the triaxial type chamber, incremental load device, triaxial type control panel and the flexible ring containing cylindrical specimen of soils or intermediate geomaterials or soft rock.

DETAILED DESCRIPTION OF THE INVENTION

In this application being filed by me as an applicant and sole inventor, several important items, as explained in the detailed description, have been made and added, when compared with my own patents as sole inventor, in U.S. Pat. No. 9,383,346 B2 (Gupta, 2016) filed on Mar. 17, 2015, U.S. Pat. No. 9,567,722 B2 (Gupta, 2016) filed on Jun. 3, 2015, U.S. Pat. No. 9,546,940 B2 (Gupta, 2016) filed on Jun. 1, 2016, International Application No. PCT/US2016/022136 with its WIPO Publication No. WO/2016/149128 (Gupta, 2016), and International Application No. PCT/US2016/035426 with its WIPO Publication No. WO/2016/196734 (Gupta, 2016). This application supplements the information described in the above cited patents, and several important items and provisions have been added and included in this application, to make to this application as one complete self-contained invention.

(a) Existing Test Methods for Triaxial Compression, Unconfined Compressive Strength Tests and Uniaxial Compressive Strength Tests The standard test methods for unconsolidated-undrained triaxial (UU) compression test and consolidated undrained (CU) triaxial compression test for cohesive soils are described in ASTM Designation: D2850-03a (reapproved 2007) and ASTM Designation: D4767-11, respectively. International and national organizations of various countries and nations have their own standards. These standards have been amended and are amended from time to time as needed to conform the latest research and practice. Triaxial compression tests on cohesionless soils are similarly performed either on dry or partially saturated or fully saturated cylindrical specimen generally with drainage permitted. Unconfined compressive strength tests are performed on intact, remolded, or reconstituted samples of cohesive soils in accordance with ASTM D2166 and AASHTO T208. Standard test methods for compressive strength and elastic moduli of intact rock core specimens under varying states of stress and temperatures are performed in accordance with ASTM D7012. These tests when performed with the expandable jacket 301 shall also be generally performed in accordance with the specifications described in these standards.

Figure 1A:
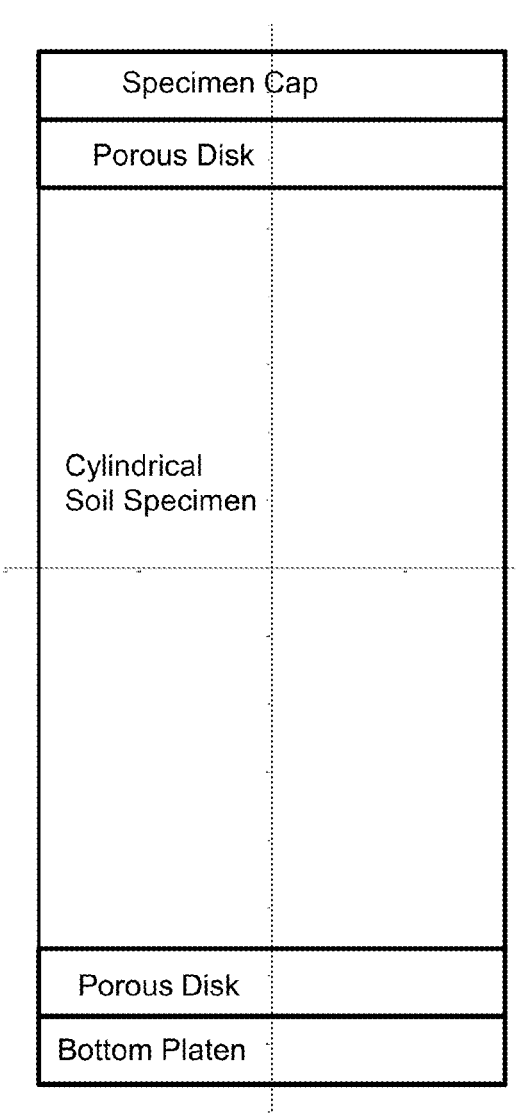
FIG. 1(a) describes the initial shape of the cylindrical soil specimen before beginning of the triaxial compression test.
Figure 1B:
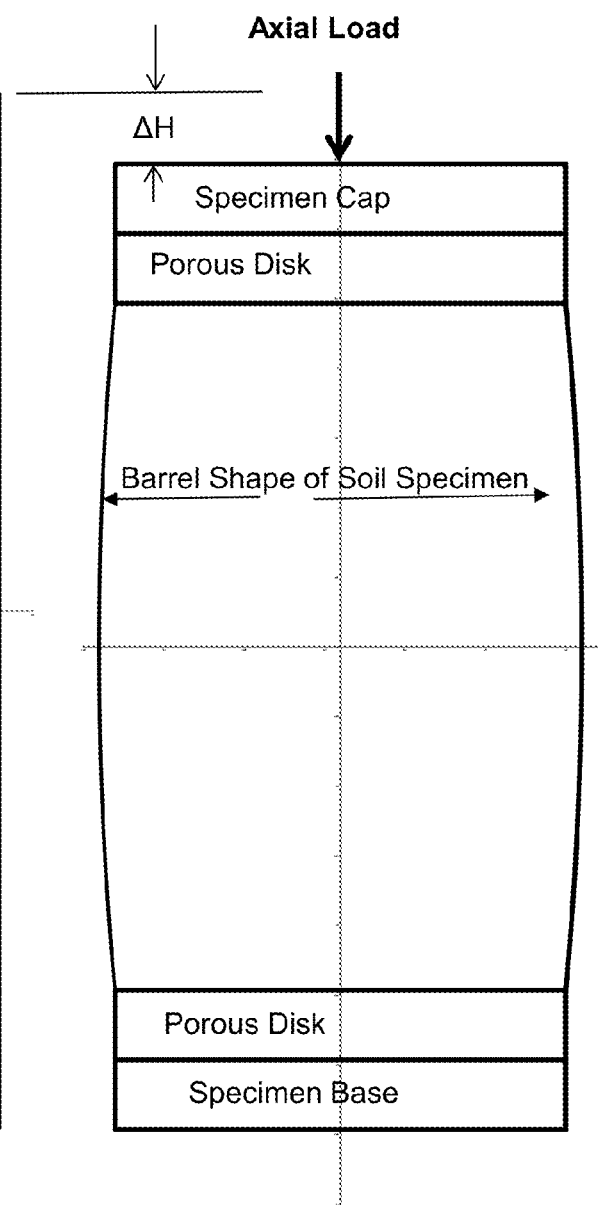
FIG. 1(b) describes the barrel shape of the same specimen with non-uniform lateral displacement during the triaxial compression test.

(b) Technical Problem with Triaxial Compression Tests and Solution to Problem Using Expandable Jacket One of the main criticisms of triaxial test is the non-uniformity of stress and deformation at all but very small strains (Rowe and Barden, 1964). The main cause of this uniformity is the friction at the end platens, which causes both the barreling effect as shown in FIG. 1A and the concentration of dilation in local zones, which results in premature development of a failure surface, as shown in FIG. 1B, although initially the specimen was of cylindrical shape. These disadvantages to some extent are largely overcome using lubricated end platens, which by removing the dead zones, allow using of short samples (Rowe and Barden, 1964). Other causes are insufficient drainage, inherent non-uniformity of soil sample through its height, membrane effects and self-weight. Question arises; how much effect does such non-uniformity have on strength, stress strain characteristics, and volume change characteristics determined from a triaxial test. Different researchers have reached different conclusions (Lee, 1978). The experimental results indicate that (i) comparison between lubricated and non-lubricated ends, shows that the end friction had little influence on measured internal friction of sand samples (Bishop and Green, 1965), (ii) the end restraint has a significant influence on undrained shear strength of sand, but slight effects on drained strength and on the internal friction angle (Lee, 1978), and (iii) the undrained strength of a dense sand tested with lubricated ends was 20% greater than that with regular ends. The fluid pressure cannot restrain the cylindrical soil specimen to maintain the uniform diameter through its height during shear, due to (1) end restraint imposed by the specimen end platens and (2) inherent non-uniformity in soil. With the result that soil specimen deforms laterally, but non-uniformly as shown in FIG. 1(b). The cross-sectional area, A, at an applied load at a time t, is calculated assuming the specimen to deform as a right cylinder with constant diameter during shear (Rochelle et al., 1988), is given by:

$$A = \frac{A_c}{(1 - \varepsilon_v)} \quad (1)$$

Where: $A_c$=Average cross-sectional area of the specimen after consolidation and before beginning the test: $\varepsilon_v$=Axial strain for the axial load at any time=$\Delta H/H$; $\Delta H$=Change in height of specimen during loading; H=height of specimen after consolidation; D=Diameter of specimen after consolidation. $\Delta V$=change in volume, V=Volume of the specimen.

When the specimen may fail, or deform by bulging with no apparent shear plane, it is generally agreed (Rochelle et al., 1988) that cross-sectional area, A, is given by:

$$A = A_c \frac{1 + \frac{\Delta V}{V}}{1 - \varepsilon_v} \quad (2)$$

It may be noted that the cross-sectional area which may govern the value of deviator stress may be controlled by the area at a height where the shearing is more intense and where slip plane may form and not necessarily by an average value, A, calculated by Eqs. 1 and 2. The expandable jacket 301 has been invented to maintain uniform radial expansion of the specimen through its height, thereby to accurately determine area of cross-section and to prevent above cited shortcomings and problems to occur in the triaxial compression tests. FIG. 2A shows the expandable jacket installed around the cylindrical specimen. The expandable jacket shall not permit the cylindrical specimen to develop a barrel shape or develop localized bulging during the test, as shown in FIG. 2B. In in-situ conditions, generally uniform lateral stiffness or confinement is provided to a soil element by the soil around it and so, when the soil element is axially loaded, it experiences vertical displacement along with uniform lateral displacement.

(c) Technical Problem with Existing Test Methods for Consolidation Tests

The standard test methods for one-dimensional consolidation properties of soils using incremental loading is described in ASTM Designation: D2435/D2435M-11 and in AASHTO 216. International and national organizations of several countries have their own standards for this test. The test apparatus for one-dimensional consolidation test consists of a rigid ring. The cylindrical specimen of soils is pushed into the ring to perform the test, creating some disturbance in undisturbed specimen, first in shaping and cutting to conform to size of the inside diameter of the fixed ring, then pushing the specimen in the fixed ring and then finally caused by some small separation initially between the cylindrical specimen and the inside surface of the fixed ring.

When foundation loads are transmitted to cohesive subsoils, there is a tendency for a volumetric strain which in the case of saturated material is manifested in an increase in pore water pressure. With sufficient elapsed time, water flows out of the soil pores, permitting excess pore-water pressure to dissipate both in horizontal and vertical directions resulting in settlements both in vertical and horizontal directions. The analysis of the volumetric strains which result, and the vertical settlements accompanying them, is simplified if we assume that such strains occur only in vertical direction. On this basis, one-dimensional consolidation tests have been conducted all these years since the 20$^{th}$ century. But In all cases, three-dimensional consolidation and settlements occur. Therefore, volumetric strains in soils significantly depend on displacements both in vertical and horizontal or radial directions.

(d) Solution to the Present Problem of Consolidation by Using Test Device for Determining Three-Dimensional Consolidation and Settlement Properties To evaluate three-dimensional consolidation properties, the inventor has invented a three-dimensional consolidation test device which permits the dissipation of excess pore water pressure both in vertical and horizontal (radial directions) directions along with displacements occurring both in vertical and horizontal (radial) directions. This device uses the flexible ring 302, which can radially expand horizontally along with simultaneous vertical settlement when the vertical load is applied, and at the same time allow dissipation of excess pore-water pressure both in vertical and horizontal directions. For determining the three-dimensional consolidation properties, tests to determine coefficient of consolidation ($c_v$) in vertical direction, coefficient of coefficient of consolidation ($c_h$) in horizontal direction and three-dimensional coefficient of consolidation ($c_{3-D}$), shall be performed. For all these coefficients, the flexible ring 302 allows the radial expansion, i.e., horizontal displacement to occur along with vertical displacement when an increment of vertical load is applied. While determining $c_v$, dissipation only in vertical direction is allowed. While determining $c_h$, dissipation in only horizontal direction is allowed. While determining $c_{3-d}$, dissipation both in horizontal and vertical directions is allowed. In all these three cases, both horizontal and vertical displacements are allowed, to occur as will happen in a field situation. For performing three-dimensional consolidation tests, there shall be some difference in the setup for determination of each coefficient of consolidation. These tests can be performed either in an open reservoir or in a triaxial type chamber or sealed reservoir. Either triaxial type loading system or incremental loading device (as normally used for one-dimensional consolidation tests) can be used along with open reservoir or triaxial type chamber/sealed reservoir.

Figure 3A:
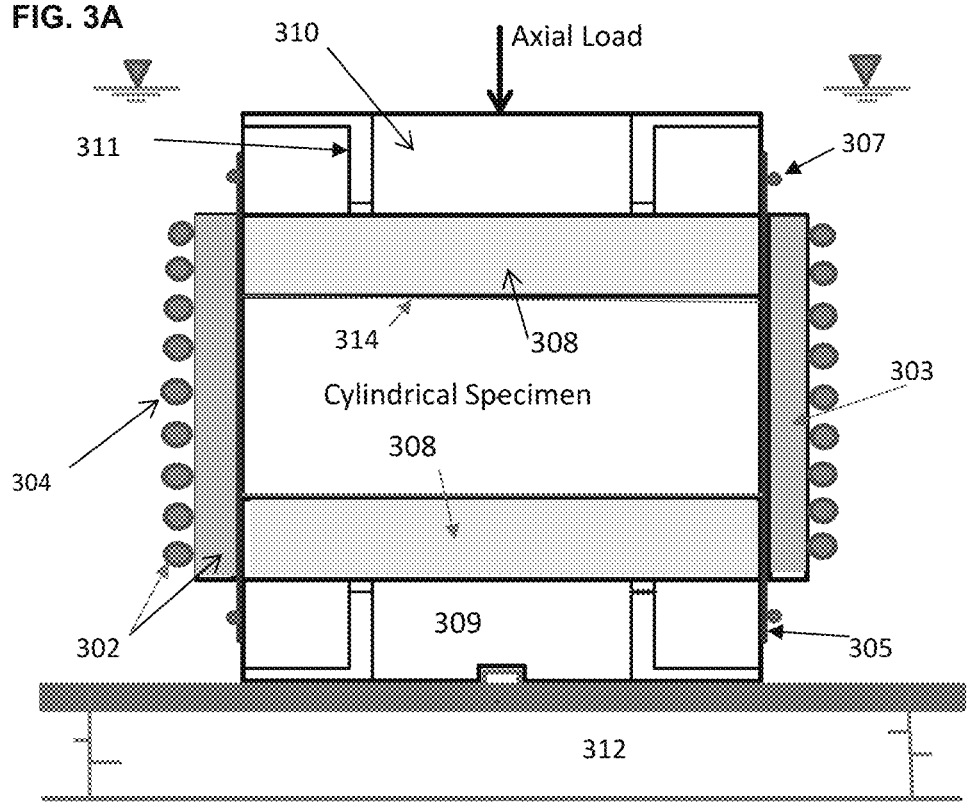
FIG. 3A shows the test device to be placed in the open reservoir for determining coefficient of consolidation in vertical direction.
Figure 3B:
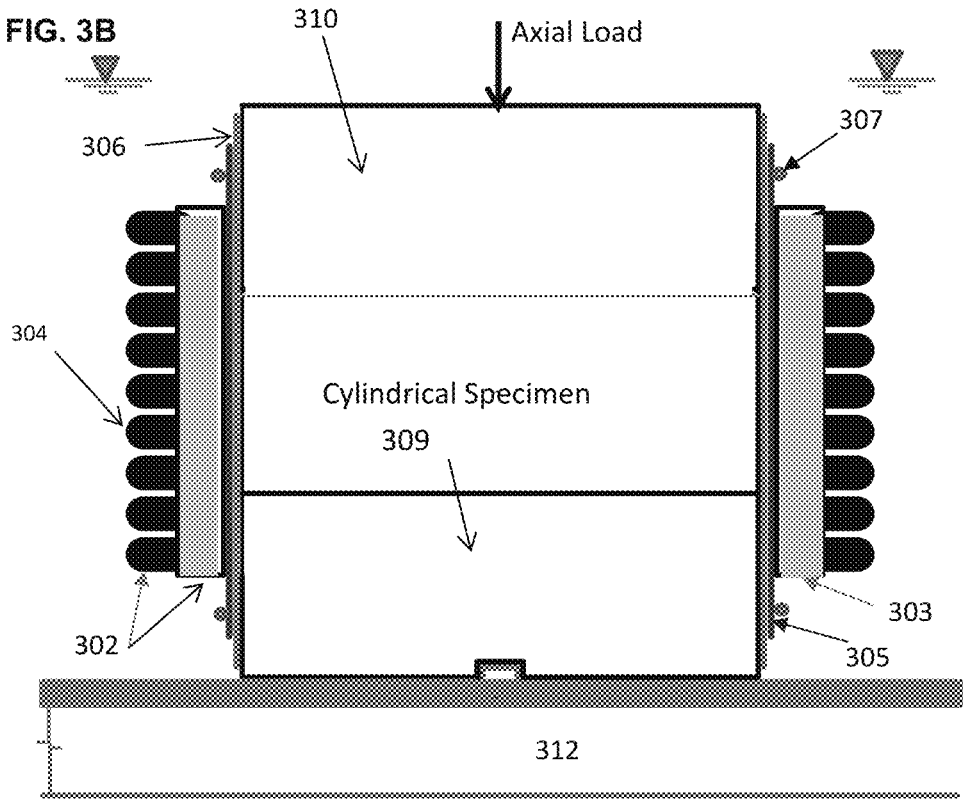
FIG. 3B shows the test device to be placed in the open reservoir for determining coefficient of consolidation in horizontal direction.
Figure 4A:
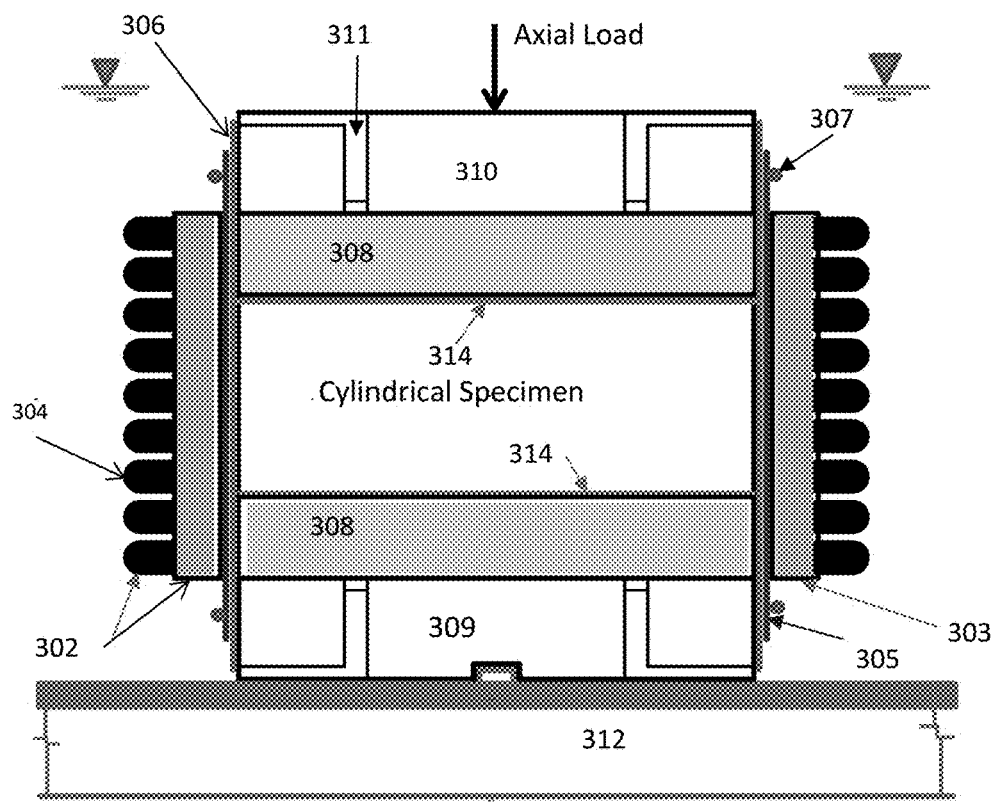
FIG. 4A shows the test device to be placed in the open reservoir for determining three-dimensional coefficient of consolidation.

FIG. 3A shows the schematic detail of a test setup for determining $c_v$. In this case filter 306 is not wrapped around the cylindrical specimen and the membrane 305 is installed directly around the cylindrical specimen. The porous disks 308 and filter disk 314 are provided below and above the cylindrical specimen. Filter disks 314 are provided to prevent clogging of porous disk 314 by fine particles of the specimen. FIG. 3B shows the schematic detail of a test setup for determining $c_h$. In this case, filter 306 is wrapped around the cylindrical specimen after which the membrane 305 is installed around the filter 306. The porous disk 314 below or above the cylindrical specimen is not provided as dissipation in vertical direction is not allowed. The filter 306 extends above and below the membrane 305 to allow flow of excess pore-water to travel horizontally to the filter 306 after which excess pore-water drains out through the filter 306 to the open reservoir. FIG. 4A shows the schematic detail of a test setup for determining $c_{3-D}$. In this case, filter 306 is wrapped around the cylindrical specimen, after which the membrane 305 is installed around filter 306. Porous disk 308 and filter disk 314 are provided both above and below the cylindrical specimen. In the test setups shown in FIG. 3A, FIG. 3B, and FIG. 4A, specimen, porous disks 314, specimen base plate 309 are placed on the bottom plate 312 of an open reservoir.

Figure 4B:
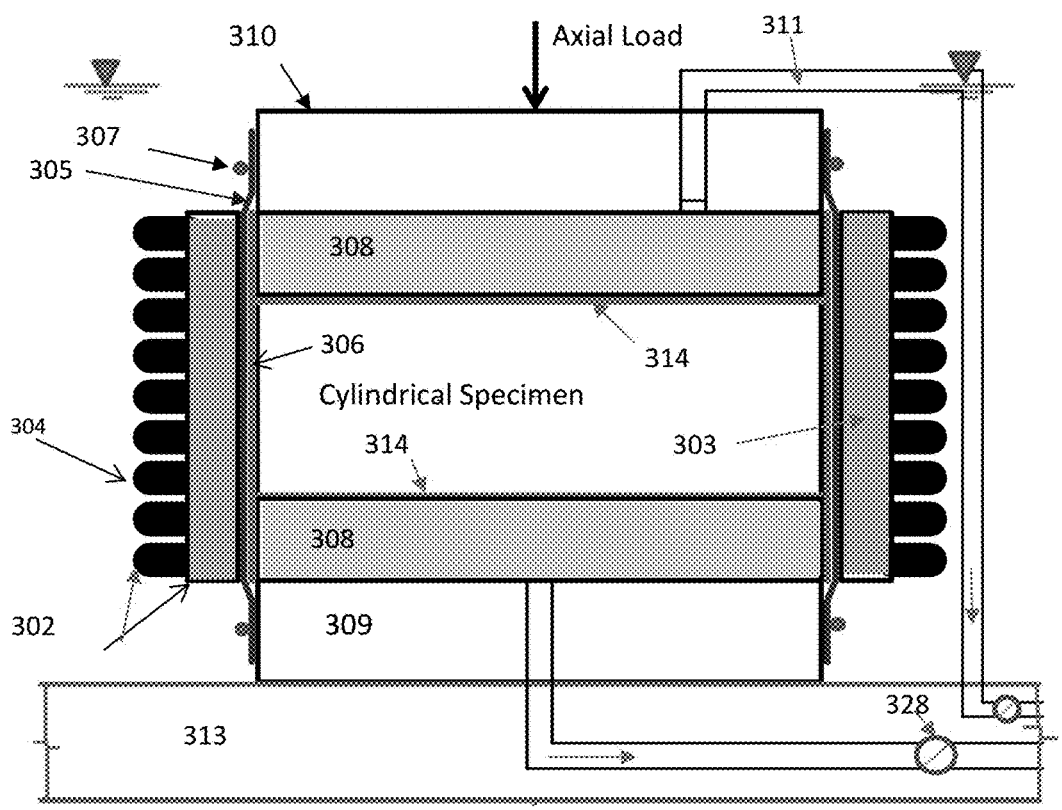
FIG. 4B to be placed in the triaxial type chamber/sealed reservoir for determining three-dimensional coefficient of consolidation.
Figure 5A:
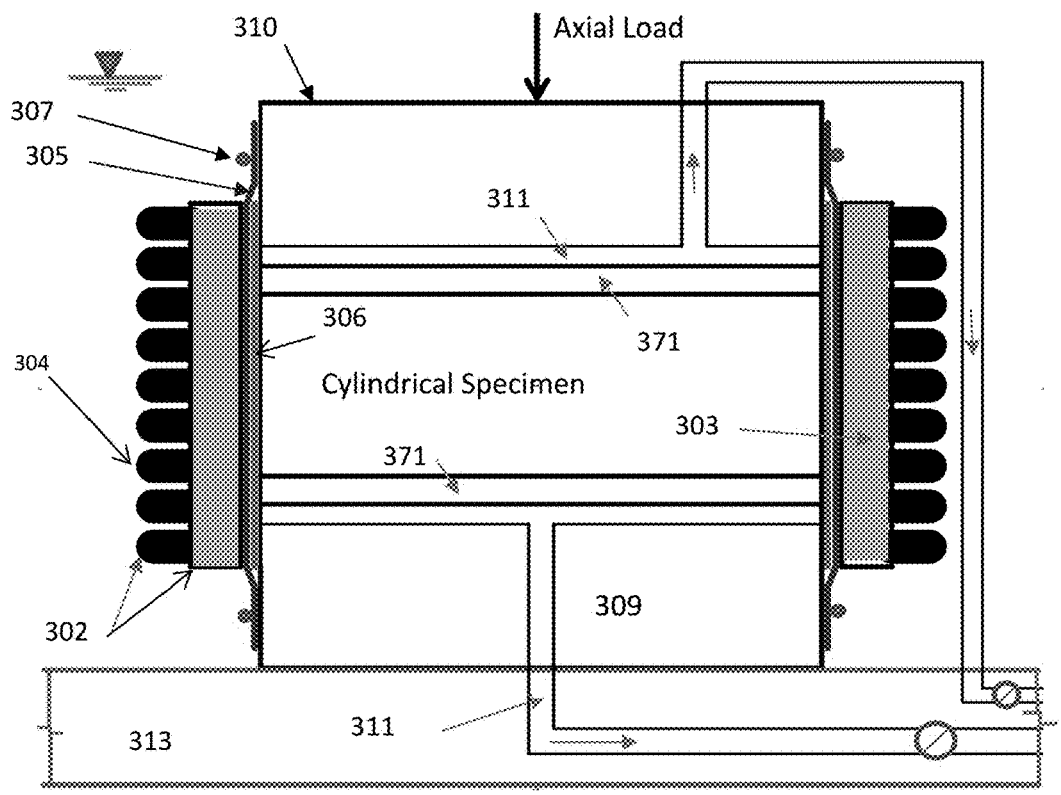
FIG. 5A shows the test device to be placed in the triaxial type chamber/sealed reservoir for determining coefficient of consolidation in horizontal direction.
Figure 5B:
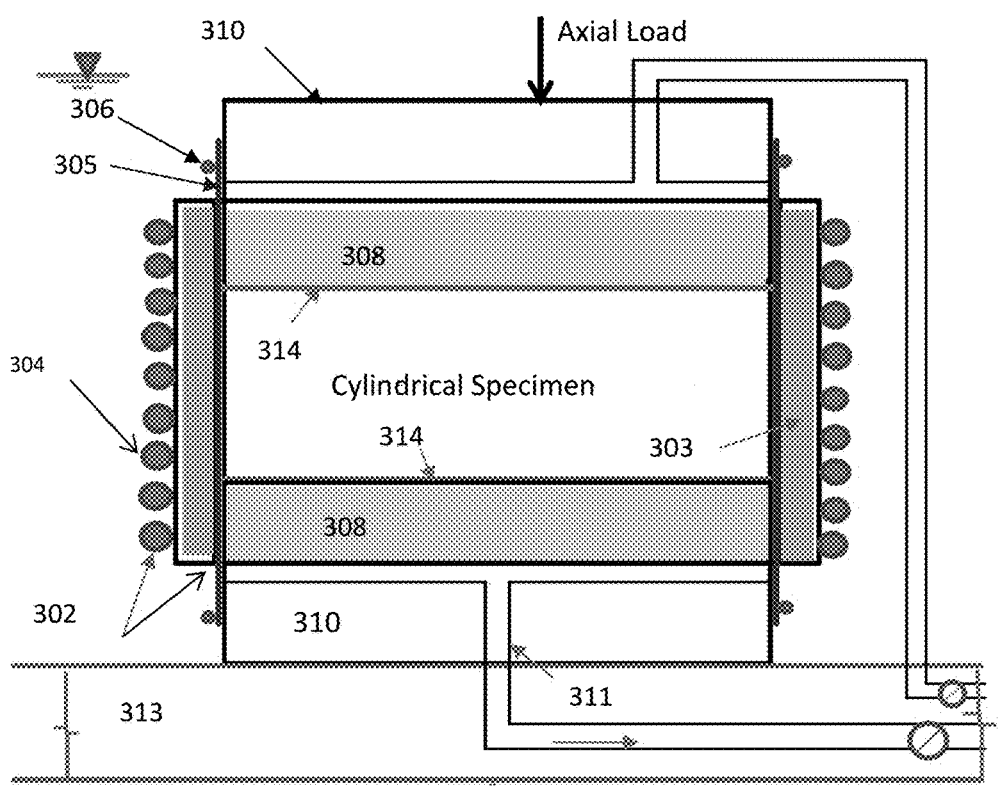
FIG. 5B shows the test device to be placed in the triaxial type chamber/sealed reservoir for determining coefficient of consolidation in vertical direction.

Other useful scheme is to perform these tests in a triaxial type chamber/sealed reservoir, to apply the lateral pressure approximately equal to the existing horizontal pressure acting at the depth from where the sample was extracted. Triaxial type control panel shall be used to monitor the excess pore-water pressures and flow of excess pore-water during consolidation. For following three cases, test setups shall be placed in a triaxial type chamber/sealed reservoir with triaxial type control panel as explained below: (i) FIG. 4B shows the schematic detail of a test setup for determining $c_{3-D}$. In this case also, filter 306 is wrapped around the cylindrical specimen, after which the membrane 305 is installed around the filter 306. Porous disk 308 and filter disk 314 are provided both above and below the cylindrical specimen. During consolidation, the excess pore-water flows out radially to the filter 306 and simultaneously flows out vertically to top and bottom porous disks, and then to drainage ports 311 in the rigid specimen cap 310 and specimen base 309, which finally leads to the control panel through valves. (ii) FIG. 5A shows the schematic detail of a test setup for determining $c_h$. In this case, filter 306 is wrapped around the cylindrical specimen after which the membrane 305 is installed around the filter 306. The porous disk 308 below or above the cylindrical specimen is not provided as dissipation in vertical direction is not allowed. An impervious rigid plate 371 is provided between the specimen and the specimen base 309 and another impervious rigid plate 371 between the specimen and specimen cap 310. The filter 306 extends to the drainage ports 311 in rigid specimen cap 310 and base 309 and the excess pore-water first travels radially to the filter 306, then filter 306 drains it out to the drainage ports 311, leading through valves to the control panel. (iii) FIG. 5B shows the schematic detail of a test setup for determining $c_v$. In this case filter 306 is not wrapped around the cylindrical specimen and the membrane 305 is installed directly around the cylindrical specimen. The porous disk and filter disk are provided below and above the cylindrical specimen. The excess pore-water flows out through porous disk 308 and then to the drainage ports 311 in the rigid specimen cap 310 and base 309 leading through valves to the control panel. In all these cases the flexible ring 302 allows the radial expansion/displacement to occur simultaneously with vertical displacement during application of an increment of vertical load.

If the field conditions are such that the drainage boundary is only at the top of the soil deposit and not below it, then the porous disk 308 shall not be provided at the bottom and the impervious rigid plate 371 shall be provided below the specimen. If the field conditions are such that the drainage boundary is only at the bottom of the soil deposit and not above the top of the layer, then the porous disk 308 at the top shall not be provided and the impervious rigid plate 371 shall be provided above the specimen. Generally, the above-mentioned tests shall be performed on the soil specimen extracted from the same Shelby tube or other undisturbed sampling methods, i.e. from the same soil strata. The tests can also be performed in remolded or reconstituted specimen of cohesive soils and intermediate geomaterials, after compacting in a split mold. Numerical analyses such as finite element or finite difference analyses based on the results of these consolidation tests can then be made accurately to determine the volume change, rate of volume change with time, horizontal and vertical displacement, rates of horizontal and vertical displacements with time, and rate of increase in vertical and horizontal stresses with time, and rate of dissipation of excess pore-water pressures, in each small soil element of the soil element matrix.

(e) Test Device to Determine Three-Dimensional Settlement Characteristics

Three-dimensional settlement tests can be performed on soils and intermediate geomaterials, which do not generate pore pressures during triaxial compression tests, using expandable jacket 301 around the cylindrical specimen at various values of fluid pressure during the triaxial compression tests. But more accurate tests can be done using the flexible ring 302 during three-dimensional settlement tests because the height to diameter ratio in triaxial tests is generally about 2, whereas the height to diameter ratio for three-dimensional consolidation and settlement tests is less than 1, generally between about 1" (25.4 mm) and 1.5" (38.1 mm), but could be as low as ½" (12.7 mm), in accordance of the standards of national organizations of various countries. The less height to diameter ratio shall avoid development of shear stresses during the tests. The test setups shall be similar-to the setups for three-dimensional consolidation tests. Since it is difficult to extract undisturbed samples of sandy samples from depths below surface in the field, the tests are generally performed on disturbed samples by compacting the soil in a mold by various compacting methods at desired densities.

The present methods of preparing reconstituted (disturbed) sand and cohesive soil shall be used for triaxial compression tests and 3-D consolidation tests. The cohesion-less soils and intermediate geomaterials is generally placed and compacted in a split-mold after stretching a stretchable impervious membrane 305 around the inner cylindrical surface of the mold; vacuum is applied by lowering a pinched tube about 2 to 3 feet (0.69 to 0.9 m) below the top of table as per prescribed procedures to stretch the membrane to form the shape of the mold. When compaction of the soil is accomplished to desired density by various methods, the stretchable impervious membrane 305 is slipped on the specimen cap 310 and specimen base 309, stretchable O-rings 307 is mounted on the stretchable impervious membrane 305 to seal it with cap 310 and base 309, then the mold is removed, the membrane 305 is kept taut by applying vacuum through a tube via bottom platen, the segmental plates are installed using the removable attachments as described here-in-after and stretchable bands or rings are slipped on the membrane 305 around the rigid segmented plates 303. Tests using either a triaxial type chamber or sealed reservoir or an open reservoir is performed using incremental loads applied by either triaxial type loading system or incremental loading system.

The test setup for three-dimensional settlement tests (for the specimen of the soil and intermediate geomaterials which either do not generate excess pore-water pressure or which dissipate as soon as the vertical load increment is applied) in the open reservoir and in chamber/sealed reservoir is the same as shown in FIG. 4A and FIG. 4B, respectively. A filter disc is placed in between the specimen and porous disks. The flexible jacket for 3-D consolidation and settlements as described above are installed using the removable attachments and if not calibrated before, then calibrated using the calibration device as described in the following sections.

(f) Expandable Jacket 301 and Flexible Ring 302 and Installation Surrounding a Cylindrical Specimen The flexible ring 302 and expandable jacket 301 for installing around the cylindrical specimen comprises of the segmented circular arch shaped plates placed vertically around the cylindrical specimen after which stretchable bands or rings 304 are installed around the segmented plates 303. The segmented circular arch shaped plates 303 as shown in figures shall be sufficiently thick and strong so as not bend but remain vertical with the lateral and flexible support provided by the stretchable and flexible bands or rings 304, when increments of a vertical load (V) are applied on the specimen during the tests. The stretchable bands and rings 304 shall be of different widths or diameters or shapes and thicknesses, depending upon the amount of lateral support needed for the segmented plates to remain vertical during the tests. A single stretchable band to cover the whole specimen can also be used. The modulus of elasticity of stretchable bands and rings 304 is also a very important factor. The modulus of elasticity of the stretchable bands and rings 304 as presently available in the industry generally varies between 50 psi and 800 psi (345 and 5515 kPa) or greater. When higher lateral support to the vertically mounted segmented plates 303 and the specimen is needed during the tests, stretchable bands or rings 304 with higher value of modulus of elasticity is preferred. The number of bands or rings used around the specimen shall be selected based on the value of lateral support required for the segmented plates 303 surrounding the specimen both initially before and later during the application of vertical load increments during tests. The inside surface of the segmented plates 303 are lubricated to reduce friction between the membrane 305 and the segmented plates 303.

Since the segmental circular arch shaped plates 303 are resting against the top and bottom porous disks 308, initially the lateral load exerted by the bands or rings 304 acts on the porous disks 308 and very little, if any, directly on the soil specimen in the beginning of the test. When specimen begins to undergo lateral displacement or radial expansion under the vertical load applied on the specimen during test, the bands or rings 304 around the segmented plates shall stretch and exert pressure on the segmental plates 303 thereby on the surface of the specimen all along its height and shall help in maintaining the uniform radial expansion through its height during the test; the plates are then not in contact with the porous disks 308 or specimen cap 310 and base 309 and therefore the stretchable bands or rings 304 exert lateral pressure on the specimen. The strength and number of rubber bands 304 should be selected in such a manner that the increase in lateral resistance is approximately equal to the increase in the calculated lateral pressure that will occur when the soil undergoes expansion of cavity or lateral displacement due to the application of load at the depth for which test is being conducted. The lateral fluid pressure in the chamber or open reservoir should be approximately equal to the insitu earth pressure from where the sample was extracted.

For performing the triaxial compression, unconfined compressive strength, and uniaxial compression strength tests, the specimen is generally prepared and installed in the test device as applicable in accordance with ASTM standards and standards of national organizations of various countries and organizations in force during the period the tests are being performed. The main difference between one-dimensional (1-D) consolidation and three-dimensional (3-D) consolidation tests is that the 1-D consolidation tests uses fixed ring whereas 3-D consolidation tests uses flexible ring, therefore it is expected the test preparation and testing methods for both 1-D and 3-D consolidation tests will generally be the same in accordance with the ASTM standards and standards of national organizations of various countries in force during the period the tests are being performed, unless the continued research and testing of various materials requires amendments or changes in the test preparation and test procedure. Test preparation generally includes (i) placing a porous disk 308 on the specimen rigid base 309, placing a filter disk 314 between the specimen and the bottom (first) porous disk 309, placing the filter disk 314 between the specimen and top (second) porous stone 309, placing the rigid specimen cap 310 on the porous disk 314, installing a stretchable impermeable membrane 305 either surrounding the specimen or surrounding the filter which is surrounding the specimen, placing at least one stretchable O-ring around the membrane 305 to hold it taut and seal on the rigid base 309 and rigid specimen cap 310, and after which the expandable jacket 301 or flexible ring 302 consisting of segmented plates 303 installed around the membrane 305 and then installing stretchable bands or rings 304 surrounding the segmented plates 303. Stretchable bands or rings 304 around the segmented plates 303 permit uniform radial expansion of the specimen while applying lateral pressure on the segmented plates 303 to maintain them in vertical position. Other steps as per the standard procedures are followed prior to performing the test.

For unconfined compressive strength of soils using expandable jacket 301, the filter around the specimen is not placed and membrane is installed directly around the specimen. Sometimes but not always, during consolidation-undrained or consolidation drained (CU or CD) triaxial compression tests, to speed-up the consolidation, filter strips are placed around the specimen and then the membrane 305 around the filter strips is installed according to ASTM standards. For unconfined compressive strength tests using expandable jacket 301, the porous disks 308 below and above the specimen may be used or may not be used. During unconfined compressive strength tests with the expandable jacket 301 around the specimen, some confinement by the expandable jacket 301 is provided. The expandable jacket 301 and the flexible ring 302 is generally installed using the removable attachments.

To prevent intrusion of material into the pores of the porous disk, a filter screen/filter disk 314 is placed between the porous disk 308 and the specimen. If filter screen/filter disc 314 is not provided to avoid its effect on compressibility of the specimen during the tests, then porous disk 308 should be cleaned occasionally by water jets or air jets and if necessary boiled in water and then cleaned again. The filter disks 314 should be of the same dimension as the cross-section of the test specimen. For 3-D consolidation tests to determine three-dimensional coefficients of consolidation and coefficient of consolidation in horizontal direction, the filter 306 is wrapped around the cylindrical specimen as shown in FIG. 4A and FIG. 4B. It is desirable to use a stretchable and flexible filter 306 in a form a cylindrical shape and installed around the specimen preferably using a membrane stretcher. A non-stretchable filter fabric formed in a cylindrical shape by stitching narrow strips of the stretchable fabric strips vertically to the non-stretchable filter fabric at least at one location (or up to 4 locations if necessary) will also become stretchable and can be installed around the specimen preferably using the membrane stretcher. The filter can also be wrapped around the specimen with an overlap and held together by a stretchable adhesive tape at the overlapping ends. The filter 306 around the specimen should/shall provide effective drainage of expelled pore-water during consolidation of the specimen to flow out vertically within the filter up and down to the outlet drainage ports 311, leading to the control panel. If necessary, a double layer of filter 306 around the specimen may be provided for effective drainage. The compressibility of the filter is checked/calibrated by a calibration device including calibration of all components of the flexible ring 302 and expandable jacket 301 to apply corrections to the deviator stress, and for determination of the modulus of elasticity of the membrane 305, and the filter 306 and the combined modulus of elasticity and lateral resistance of the expandable ring 301 and the flexible ring 302 as explained here-in-after.

When using the expandable jacket 301 and the flexible ring 302, it is very important that the membrane around the porous disks 308 and specimen cap 310 and base 309 remains tightly in contact during the tests, and does not form any gap between membrane 305 and the porous disks 308, for preventing migration of soil from the specimen towards the porous disks and any possibility of intrusion of soil of the specimen between the membrane 305 and the porous disks 308. For this purpose, in addition of O-rings, a band or membrane of sufficient width may be provided surrounding the O-rings and bottom porous disk 308 and surrounding the O-rings and the top porous disk 308, unless tests indicate that the single membrane 305 surrounding the specimen and porous disks 308 is safeguarding sufficiently to prevent any separation between the membrane 305 and porous disks. A stretchable or un-stretchable removable adhesive tape can also be wrapped around the porous discs and O-rings to prevent any migration of soil from the specimen to between membrane and porous disks. Using a membrane stretcher, the stretchable and impervious membrane 305 shall be installed. A thicker stretchable membrane 305 which can be installed using a membrane stretcher or other appropriate device, shall have some advantage over thinner membrane 305 as a thick stretchable membrane 305 shall keep the cylindrical shape along the joint space between the segmented plates 303 and will not permit any gap to form between the membrane 305 and the porous disks 308. If necessary two membranes in place of one may be installed around the specimen, porous disk and specimen cap and base.

The diameter and height of the cylindrical specimen is selected based on the local practice or based on standards of international organizations or national organizations of each Country/Nation. Sizes (diameter and height) and number of sufficiently rigid and strong segmented plates, half brackets and sizes (diameter and thickness or width and thickness) of stretchable bands or rings shall depend upon the diameter and height of the specimen. For a good design and performance, it is expected that the number of vertically the segmented plates shall vary between about 6 and 12 for specimen diameters of between about 2.5" (63.5 mm) and 3" (76.2 mm). Diameter of the soil specimen may vary generally between 1.5" (38 mm) and 4" (100 mm). Number of segmented plates may generally vary between about 4 and 20 for soil specimen of diameters between 1.5" (38 mm) and 6" (152 mm), respectively. For other specimen sizes, special design for segmented plates, bands or rings, brackets and straps shall be used.

As described above, the expandable jacket 301 and flexible ring 302 shall maintain cylindrical shape of the soil specimen and its diameter shall remain uniform through its height during the test. Near the bottom and top porous disk, the diameter of specimen shall transition from diameter of porous disk 308 to the expanded diameter of the specimen. Height of the transition shall be expected to be about two times of the increase in radius of soil specimen as load distribution occurs at 1H:2V in accordance with accepted theories. It has been estimated that height of transition is very small, varying between 0.042" (1 mm) to 0.14" (3.6 mm) for axial strains between 1 and 10% (Gupta, 2016). Through the remaining height of the soil specimen, the expandable jacket 301 shall succeed in maintaining cylindrical shape with uniform diameter. The lateral stress exerted by the bands and membrane shall be a product of lateral strain and modulus of elasticity of stretchable bands and rings 304. It has been estimated that the lateral stress, exerted by the stretchable membrane 305 and bands and rings 304 on the soil specimen, may vary from 0.3 psi at 1% axial strain to 4.5 psi at 15% axial strain for sand specimen with Poisson's ratio of 0.3. The lateral stress exerted by the membrane and bands and rings 304 may vary from 0.5 psi at 1% axial strain to 7.5 psi at 15% axial strain for saturated clay specimen with Poisson's ratio of 0.5. The above calculations are based the value of modulus of elasticity of 100 psi (689 kN/m$^2$) for the membrane, bands or rings (Gupta, 2016). Expandable jacket 301 and flexible ring 302 helps to maintain cylindrical shape with uniform diameter and helps to quantify the lateral strain and lateral stress exerted by the rubber bands and membrane accurately. Note: 1 psi=6.894757 kN/m$^2$, 1"=25.4 mm, 1 foot=0.3048 m.

The Undisturbed samples of cohesive soils and intermediate geomaterials can be extracted using the existing methods from the subsurface at the selected depths and tests performed for triaxial compression, 3-D consolidation and unconfined compression tests using the expandable jacket 301 or flexible ring 302. Undisturbed samples of cohesionless soils cannot be extracted from subsurface from any depth, unless the soil is frozen in advance by well-known freezing methods at the depths from where samples are to be extracted. Remolded/recompacted specimens for cohesive soils when necessary for embankment fills etc., are prepared in the laboratory and these tests performed, using expandable jacket 301 and/or flexible jacket 302. The remolded specimen of cohesionless soils are prepared in molds using existing procedures of the testing methods, after which the triaxial compression, unconfined compression and 3-D settlement tests are performed on remolded samples.

When expandable jacket 301 is used, triaxial compression tests on soils and intermediate geomaterials can also be performed without chamber or fluid pressure in the chamber, but applying lateral stress on the specimen by the stretchable bands or rings 304 on the segmented plates 303. These tests can be performed at various values of lateral stress by selecting and varying number of bands or rings, their size and modulus of elasticity, for determining the angle of friction, undrained and drained strengths, Mohr's circles, $K_f$-line and Coulomb failure envelope. With this approach, since no fluid pressure shall be used, even a triaxial chamber shall be unnecessary. The triaxial tests on dry or partially saturated soils and consolidated drained tests on cohesive soils (without performing the procedure for back saturation of the specimen) which will not generate pore-water pressures shall be appropriate to perform with expandable jacket 301 without use of triaxial chamber and control panel. The specimen base and cap with valves as used with the triaxial chamber shall be preferable. The present methods for preparing reconstituted (disturbed) sand specimen and cohesive soil samples can be used. These tests can be performed with or without using LVDT for measuring the radial expansion of the specimen.

(g) Removable Attachments for Installing Expandable Jacket 301 and Flexible Ring For installation of the expandable jacket 301 and flexible ring 302, suitable removable attachments should be used. FIG. 6A and FIG. 6B shows use of half-circle shaped brackets to install the expandable jacket 301 and flexible ring 302. FIG. 7A shows the sufficiently strong segmented circular arch shaped plates 303 installed in proper configuration by using removable two half-circle shaped brackets 318 around the membrane 305. The brackets 318 shall be sufficiently strong and rigid to maintain circular shape during installations as well as during the time when not in use. First the segmented plates 303 are attached to each half-circle shaped bracket 318 by using screws 315 on screw mounts (threaded holes) or snap on pins on unthreaded holes at predetermined heights of the segmented plates 303. Each of the half brackets 318 with attached segmented plates 303 are installed around the membrane 305 containing cylindrical specimen and then the two half-circle shaped brackets 318 are fastened together at their ends by screws 317. The next step is to install bands or rings 304 around the segmented plates as shown in FIG. 7A. After installation of bands or rings 304, the removable attachments consisting of brackets 318 are removed as their intended purpose has been achieved and in the space previously occupied by the brackets 318, the additional bands or rings 304 are installed around the segmented plates 303 as shown in FIG. 7C. FIG. 7A and FIG. 7B also show additional screw mounts 322 for using additional brackets or hook and loop straps, if so needed for proper installation.

Removable attachments using hook and loop straps 323 shall also be used in addition or in combination or in place of the half-circle shaped brackets 318. The straps have holes to pass through the screws. The segmented plates 303 are fastened to Hook and loop strap or straps at predetermined heights, using appropriate size screws 315 or snap on pins. For snap on pins, unthreaded holes shall be used. Then the assembled segmented plates 303 are wrapped around the cylindrical specimen and maintained in vertical position by hook and loop straps, after which bands or rings 304 are installed around the plates as shown in FIG. 7B. After proper installation of flexible ring 302 or expandable jacket 301, the straps are unfastened and removed as their intended purpose is completed, and the additional bands or rings are installed around the segmented plates as shown in FIG. 7C.

For using the removable attachments as described above, the segmented plates 303 shall be provided with threaded holes (screw mounts) at predetermined heights. To avoid providing screw mounts in the segmented plates, another scheme of removable attachments can be used using hook and loop straps 323. A small piece of hook strap 324 or 325 with removable adhesive base shall be placed at predetermined heights of each segmented plate 303 as shown in FIG. 8A. A loop strap 326 with a piece of hook strap 324 stitched to it at one end or a hook strap 327 with a piece of loop strap 325 stitched at one end, shall fasten all the segmented plates together when the straps are installed on the pieces of adhesive hook straps 324 or lop strap 325 as shown in FIG. 8B. The assembled segmented plates 303 using the above scheme are then installed around the membrane 305 containing the specimen and the hook and loop straps fastened together. The next step is to install bands or rings 304 in the space not covered by the hook and loop straps, after which the removable attachments comprising hoop and loop straps and all the pieces of the hook straps or loop straps are removed as their intended purpose has been achieved. The additional bands or rings 304 are installed in the space earlier covered by the removable attachments. The scheme then becomes about the same as the scheme shown in FIG. 7B and FIG. 7C. Other simpler method is not to place the adhesive pieces of hook of loop strap, but assemble segmented plates 303 using the removable adhesive hook and loop straps sticking directly on the segmented plates 303 as shown in FIG. 8C. After installing the assembled the segmented plates surrounding the membrane containing the specimen, bands or rings 304 are installed around the segmented plates 303. The scheme then again becomes as shown in FIG. 7B and FIG. 7C.

Figure 9A:
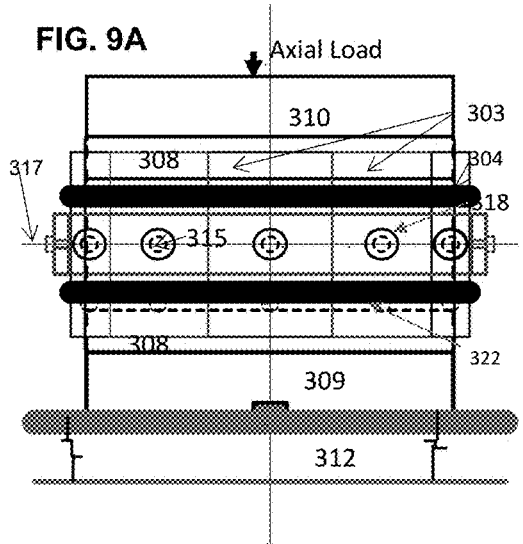
FIG. 9A shows the elevation view of the flexible ring 302 installed surrounding the membrane 305 containing the specimen using half-circular shaped brackets 318.
Figure 9B:
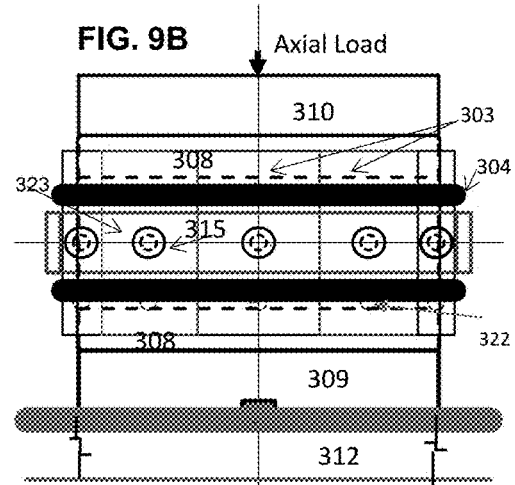
FIG. 9B shows the elevation view of the flexible ring 302 installed surrounding the membrane 305 containing the specimen using hook and loop straps 323.

FIG. 9A and FIG. 9B show the installation of the flexible ring 302, using the two half-circle shaped brackets 318 or hook and loop straps 323 or both brackets and hook and loop straps in combination, at least at one predetermined height.

(h) Radial Expansion or Displacement During the Triaxial Compression and Three Dimension Consolidation and Settlement Tests The determination of the value of radial expansion of the cylindrical specimen during the triaxial compression tests is generally not an issue and generally have been seldom done, as the cylindrical specimen forms a barrel shape during the tests. The one-dimensional consolidation tests are performed in fixed ring permitting no radial expansion of the specimen. However, when the expandable jacket 301 or flexible ring 302 is used, it becomes important to calculate or measure the value of the radial expansion during the test. Based on the value of radial expansion, the value of radial strain and the value of additional lateral stress exerted by the membrane 305 and bands or rings 304 on the cylindrical specimen is calculated for applying correction to the deviator stress during the triaxial compression test and to determine the lateral stress exerted by bands or rings 304 during 3-D consolidation and settlement tests.

The lateral radial expansion/displacement of the 100% saturated soil specimen can be calculated based on the excess pore-water expelled out from the specimen during the consolidation phase and measured in the burette located in the triaxial type control panel or measured by other devices or electronic devices, and change in the height of the specimen. For dry or partially saturated soils, the radial expansion of the specimen can be approximately calculated based on the value of Poisson's ratio for various types of soil as available in the publications or guidelines and vertical displacement measured during the test. Poisson's ratio is the ratio of radial strain with vertical strain of the cylindrical specimen. Radial strain is equal to the ratio of change in diameter divided by the diameter. Vertical strain is the ratio of change in height divided by its height. More accurate values of Poisson's ratio shall be available after tests using the expandable jacket 301 and flexible ring 302 have been performed and published. LVDTs or strain gages to measure the radial expansion during the tests on dry or partially saturated soils and 100% saturated soils shall also be used when considered important for the accuracy of measurements. For some laboratories, it may be found useful to perform the triaxial compression and 3-D consolidation tests without the measurements of radial displacement by LVDT or strain gages and calculate approximately the radial displacement as explained above. Therefore, all these tests can be performed with or without the measurement of radial displacement by LVDT or strain gages.

Unconfined compressive strength tests on soft and jointed rocks when using the expandable jacket 301 can be performed with or without the membrane 305 surrounding the specimen. Uniaxial compression strength tests on concrete core and intact rock cores can be performed with or without expandable jacket 301. LVDT measurements can also be done for these tests to determine accurately the area of cross-section, compressive strength, Poisson's ratio and modulus of elasticity.

(i) LVDTs and Strain Gages for Measurement of Radial Expansion and Mounting Devices There are several types of LVDTs and strain gages which are available in the industry. LVDTs are generally available in stroke ranges ±0.25 inch (±6.35 mm) to ±1 inch (±25.4 mm) with imperial or metric cores. The length of the body 339 of LVDTS vary from approximately between about 3 to 8 inches (76.2 and 200 mm) depending on the stroke length, although miniature LVDTs are also available in much shorter body lengths. The spring loaded LVDT or guided core LVDT which are not generally water resistant cannot be used under water such as in the open reservoirs or in the pressurized water chambers/sealed reservoirs, but can be safely used for unconfined compressive strength and uniaxial compressive strength tests. High pressure sealed and hermetically LVDTs are available in the industry for displacement measurements in the pressure sealed chambers, hydraulic actuators and pressure vessels, which are generally constructed with heavy-wall 304 series stainless steel. All welded LVDT is highly resistant to corrosive environments. These LVDTs are suitable to very high pressures far exceeding 500 to 1000 psi. Generally, sealed LVDTs are not spring-loaded. The LVDTs have either radial or axial connectors.

Figure 10:
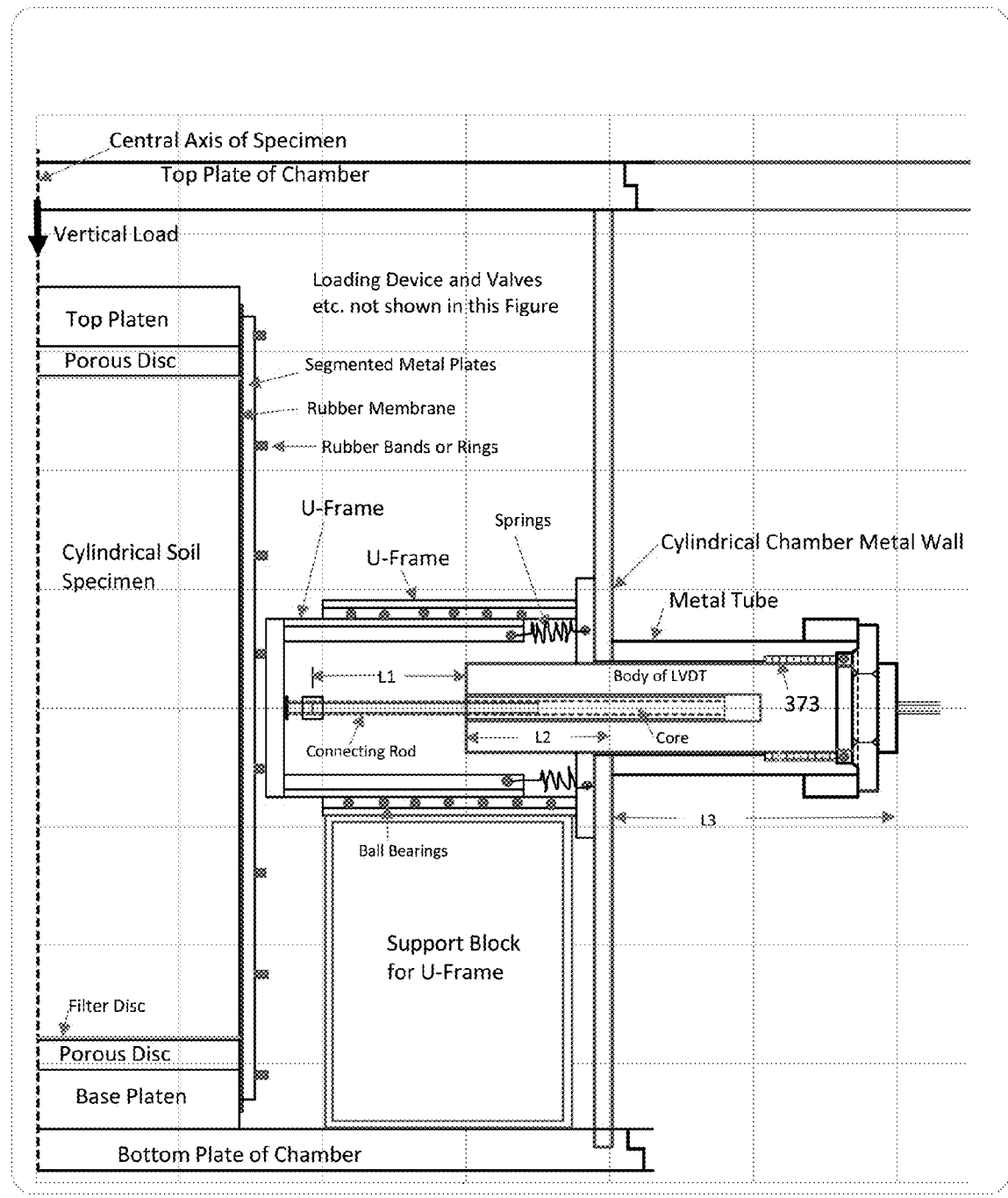
FIG. 10 shows a typical section with details of LVDT with axial connector and U-frame 340 and facing plate 372 of U-frame in contact with bands or rings 304 of expandable jacket 301 when whole assembly placed in a triaxial chamber.

There is a high pressure sealed LVDT and the axial connector with a threaded end 373 has a shape according to manufacturer's diagram and can exit with a sealed exit from the pressure chamber. A metal tube 330 is weld connected to the metal cylindrical wall of the chamber. Metal tube 330 has female threads matching with the male threads of the connector; the O-ring seals the exit, as shown in FIG. 10. The shape of the LVDT shall be in conformance with the manufacturer's diagram. This LVDT is attached to the U-Frame 340 loaded with springs 341. At the end of the metal tube 330, another metal tube 330 around it is weld connected. The outside vertical surface of both metal tubes 330 is machine finished and polished to a very smooth surface. The core 337 of the LVDT is inserted in the body 339 of LVDT, and generally positioned so that the outside of the face of the core 339 approximately match with the inside face of body 339. The connecting rod 336 is thread connected to the core 339. The other end of the connecting rod 339 is thread connected to the facing plate of U-frame 340. As shown in this figure, L1 is the length of the connecting rod 336 outside the face of the LVDT, L2 is the LVDT body 339 inside the chamber, and L3 is the length of the LVDT body 339 outside the metal wall of the cylindrical chamber 338. For the same size specimen, outside diameter of the expandable jacket 301 or flexible ring 302 and inside diameter of the metal chamber 338, Lengths L1 and L2 can remain same, but Length L3 can vary depending on the length of the body 339 of LVDT. The length of the LVDT body 339 is governed by the length of the stroke. Greater the stroke length, greater is the length of the LVDT body 339 and therefore greater will be Length L3. If necessary, another O-ring may be provided at the other end of the threaded portion 373 or threads wound around by polytetrafluoroethylene (PTFE) for additional insurance for waterproofness. FIG. 10 has been drawn for triaxial compression tests. The FIG. 13 for the above LVDT has been drawn for the 3-D consolidation tests.

Figure 11:
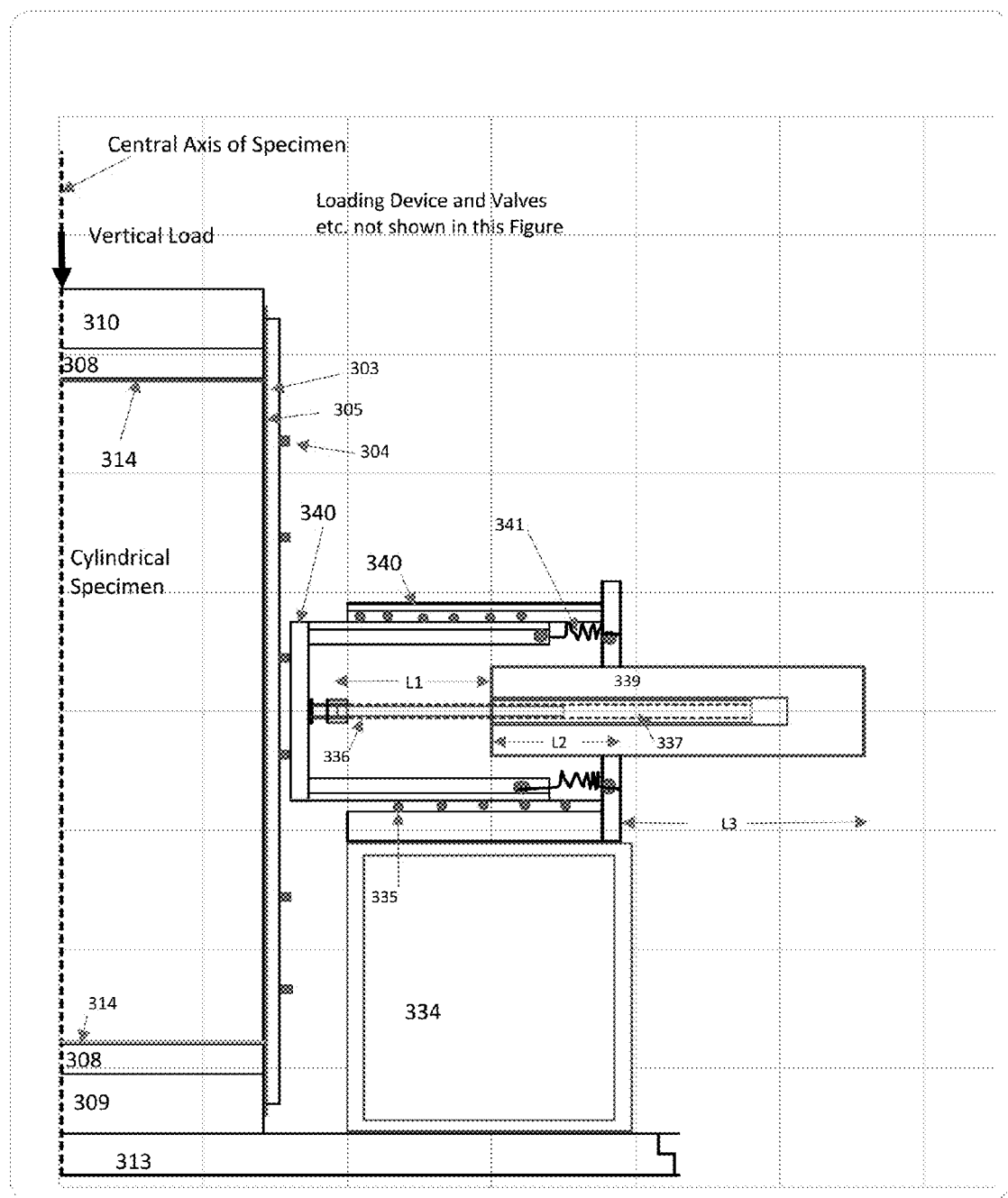
FIG. 11 shows a typical section with details of LVDT and U-frame 340 and facing plate 302 of U-frame in contact with bands or rings 304 when measuring the radial displacement during unconfined compressive strength test.
Figure 12:
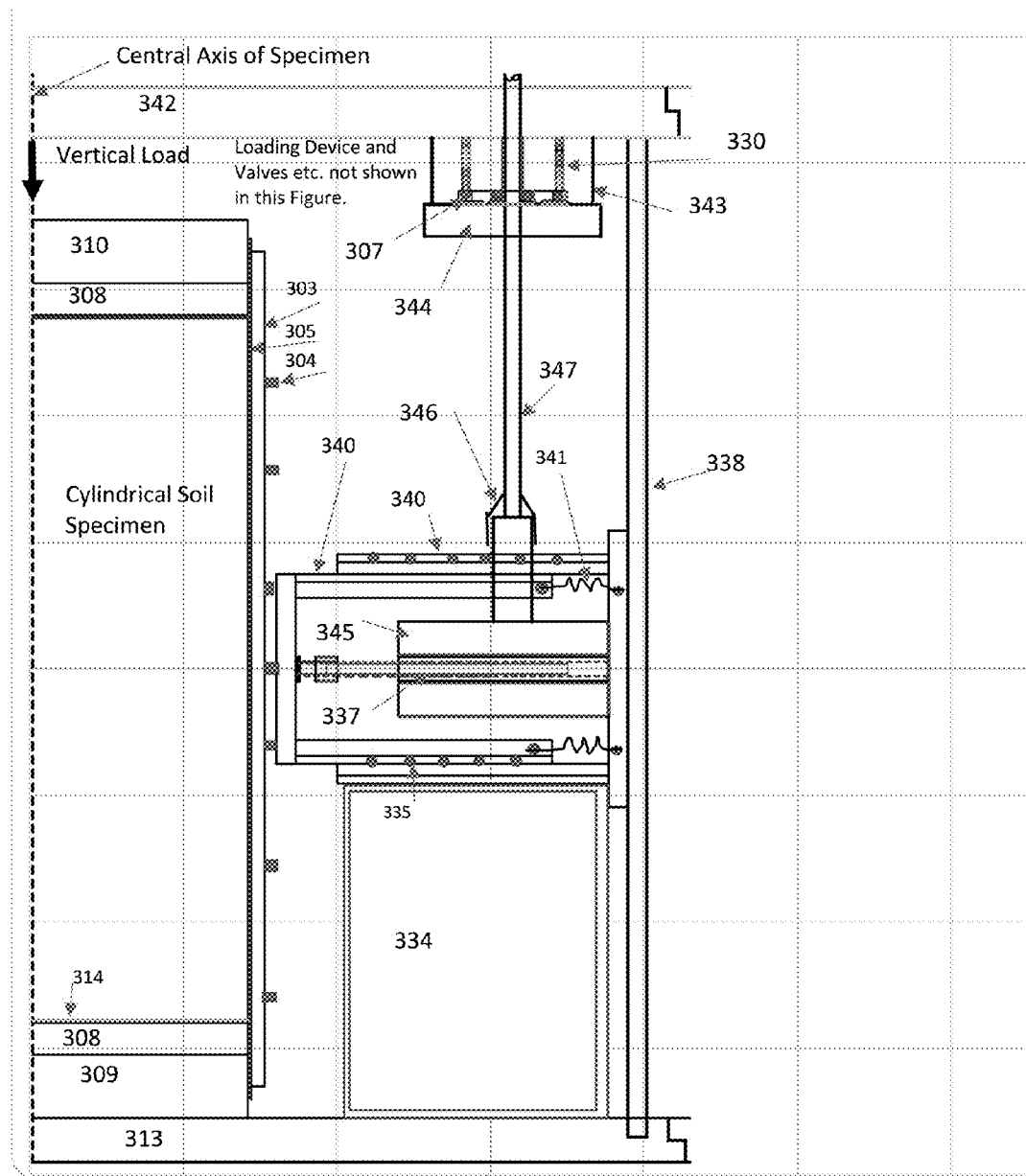
FIG. 12 shows a typical section with details of LVDT with radial connector and U-frame 340 and facing plate 302 of U-frame in contact with bands or rings 304 of expandable jacket 301 when whole assembly placed in a triaxial chamber.

FIG. 11 and FIG. 12 show a typical detail of the LVDT removably attached to the spring-loaded U-frames for the measurement of radial expansion during unconfined compression tests and for the uniaxial compression strength tests on the concrete core and intact rock core, respectively. Guided core LVDT is mounted in spring 341-loaded U-Frame 340. Spring loaded LVDT can be removably attached to either spring-loaded U-Frame or non-spring-loaded U-Frame for the radial measurements.

There is another hermetically sealed (i.e. high pressure sealed) LVDT in which coil windings are sealed and the axial or radial connector 342 with the main body 345 is also sealed, and the cable exit 346 from the connector and the cable 347 is also double sealed, generally using an internal gland plus a shrink tube over the connector. A specially designed sealed exit is provided from either the cylindrical wall of the chamber or from the top plate of the chamber. For LVDT with radial connector, the sealed exit for the shielded/sealed cable 347 is provided from the top plate 342 of the chamber/sealed reservoirs as shown in FIG. 12. The specially designed sealed exit as shown in FIG. 12 consists of (i) an internally threaded metal tube 330 weld connected to the top plate 342, (ii) O-rings between the shielded cable 347 and a threaded plug 343 and (ii) additional O-rings between the internally threaded metal tube 330 and threaded metal plug 343 monolithic with metal plate 344. Although the metal tube 330 is shown as weld connected at the bottom of the top plate 342 in this figure, but the metal tube 330 can also be welded at the top of the metal tube 342 with a metal cover plate 344 on the top of the metal tube and properly sealed by O-rings with a similar detail as shown in FIG. 12. If top plate is sufficiently thick, then a similar design of sealed exit can be provided through the top plate using metal cover 344 without any need of the weld connected metal tube. If taper threads or straight threads wounded by the PTFE is used, then O-ring between threaded plug and the metal tube can be avoided. For LVDTs with sealed axial connectors and sealed/shielded cable, a specially designed sealed exit with a similar detail as explained above, is provided through a metal tube weld connected to the metal wall of the chamber/reservoir. It may be observed that LVDTs with radial connectors can be exited with a sealed exit from the top plate, both for metal and acrylic cylindrical walls. For open reservoirs, this type of LVDTs shall also be used in open reservoirs to exit from top of the water.

The design detail such as the design, the shape and the length of the body and lengths of its various components of LVDT can vary from manufacturer to manufacture of the LVDT. Special design details specially for sealed exit either for the body of LVDT or its shielded cable shall be made for LVDTs available in the industry from time-to-time. Two LVDTs, each located diametrically opposite each other can also be provided to have measurements at two locations, although measurement by one LVDT could be considered sufficient. Four LVDTs located 90 degrees apart along the perimeter of cylindrical specimen can also be provided to get data of radial expansion at four radial directions.

Figure 9C:
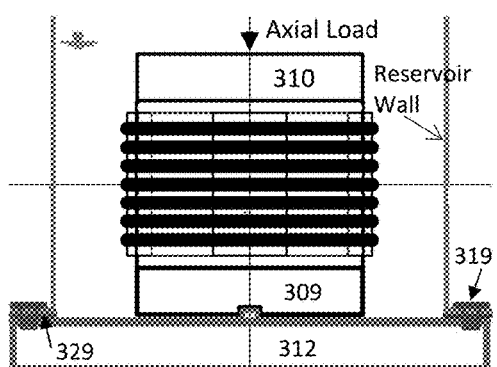
FIG. 9C shows flexible ring 302 placed surrounding the membrane 305 containing the specimen and placed in an open reservoir.
Figure 9D:
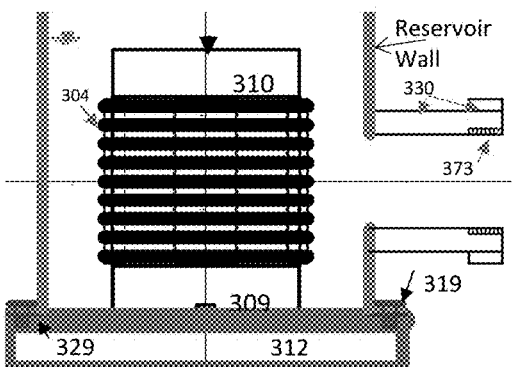
FIG. 9D shows the metal tubes 330 weld connected to the reservoir wall to receive a LVDT with axial connector.
Figure 13:
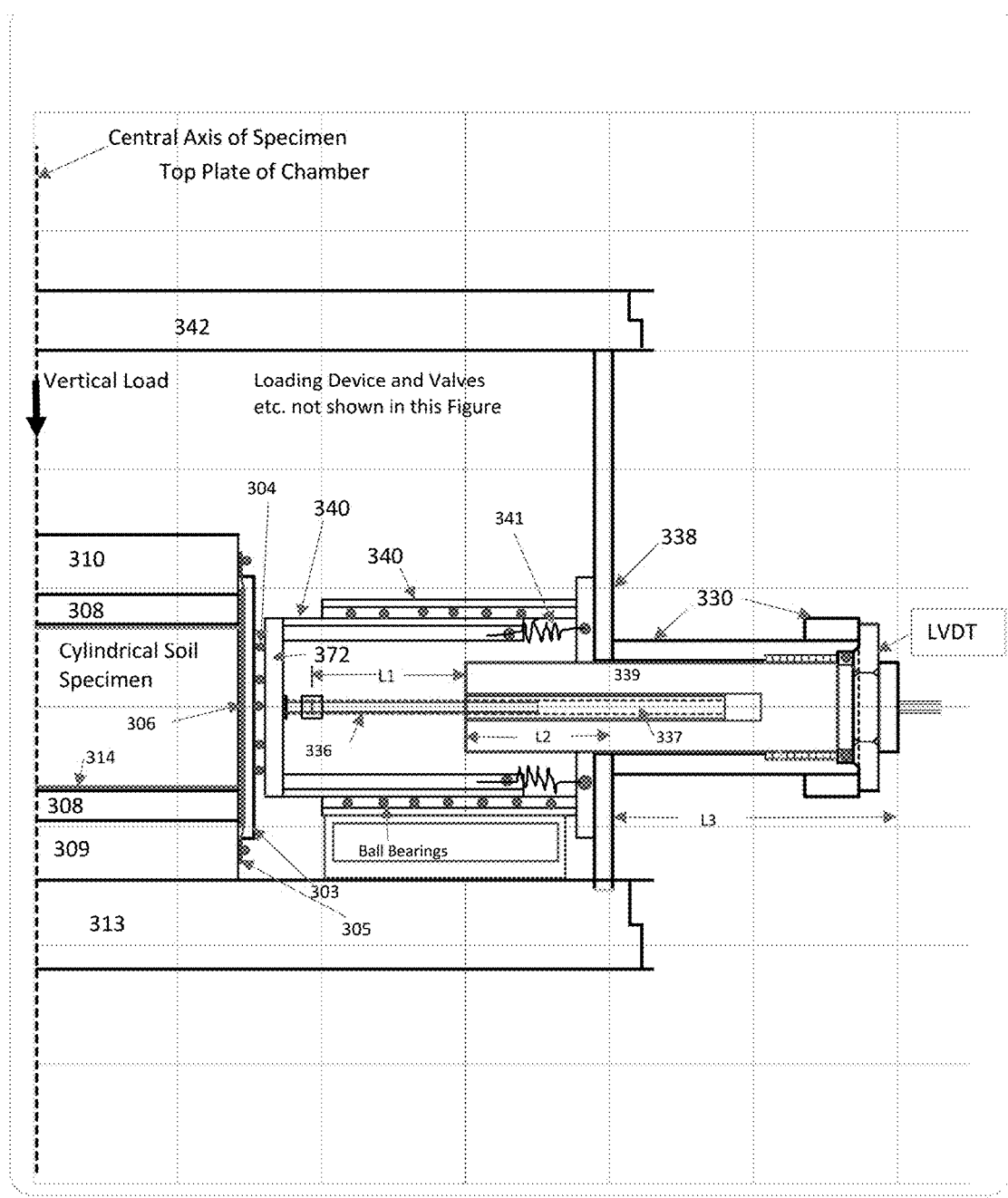
FIG. 13 shows a typical section with details of LVDT with axial connector and U-frame 340 and facing plate 372 of U-frame in contact with bands or rings 304 of flexible ring 302 when whole assembly placed in a triaxial chamber.

Hermetically sealed (high pressure sealed) LVDTs in which coil windings are sealed and the axial or radially connector to the main body of the LVDT is also sealed, but the cable exit from the connector is not sealed, can be also be used with certain precautions in the open reservoirs, such as by sealing/shielding the cable exit of the radial connector by fuse tape or double sealed using shrink tube and fuse tape so that the electronics are not damaged from the moisture or water while exiting from the water in open reservoirs. The LVDT with the axial connector of the type shown in FIG. 13 can also be used for the measurement of radial displacement of the specimen when 3-D consolidation tests are performed in the open reservoirs. The metal tube is weld connected to the wall of the open reservoir as shown in FIG. 9D and LVDT installed with similar detail as shown in FIG. 13. As mentioned earlier the 3-D consolidation tests and triaxial compression tests shall be performed with or without LVDT for measurement of the radial displacement by LVDT.

Strain gages for measurement of radial strain and displacement are custom and specially designed for these tests. Adequate precautions are taken to ensure that the electronics of strain gages are protected against the fluid pressures and moisture in the chamber/sealed reservoirs and open reservoirs. Specially designed sealed exit for the strain gages and their cables from either top plate of the chamber/sealed reservoir or from their cylindrical wall including of open reservoirs is provided.

Mounting Devices for LVDT Using U-Frames Movable on Ball Bearings

FIG. 10 shows a U-Frame 340 which slides on the ball bearings 335 both at its top and bottom. The U-frames 340 can be spring 341-loaded or not spring-loaded. The spring-loaded U-frames can be used for both spring-loaded LVDT or LVDT which are not spring-loaded, but non-spring-loaded U-frames can only be used for spring-loaded LVDTs. The facing plate 372 of the U-frame 340 is designed to keep in contact with the at least one band or ring 304 of the expandable jacket 301 or flexible ring 302 before beginning the test. If tests such as uniaxial compression tests on intact rock cores or concrete cores, which are cylindrical in shape, are being performed and expandable jacket 301 is not used, then the facing plate of the U-frame 340 is in contact with the surface of the rock or concrete core. The springs mounted in the U-frame shall maintain the initial position of the LVDT core 337 via connecting rod 336 same as at the beginning of the test. When the radial expansion of the specimen takes place during these tests, the core of the LVDT moves inside tube of the body and provides the value of radial displacement at an instant of time during the test, which is recorded and read by the LVDT signal conditioner, controller and readouts. The facing plate 372 of the U-frame is lubricated, so that it slides smoothly on the surface of rings or bands 304 of the expandable jacket 301 and flexible ring 302 surrounding the cylindrical specimen or on rock or concrete core, when the cylindrical specimen is undergoing vertical settlement due to the application of vertical load during the test. The U-frame is seated on a supporting block 334 placed on the chamber base 313. With U-Frame 340, the vertical settlement and radial expansion of the soil specimen or the rock core can occur simultaneously preventing the bending of the LVDT core and preventing the LVDT core from getting inclined due to vertical displacement while maintaining the horizontal position of the LVDT core, the connecting rod and LVDT body throughout the test.

Two LVDTs, each located diametrically opposite each other can also be provided to have measurements at two locations, although measurement by one LVDT could be considered sufficient. Four LVDTs located 90 degrees apart along the perimeter of the cylindrical specimen can also be provided to get data radial expansion at four locations. If two LVDTs are used, then two metal tubes diametrically opposite to each other shall be provided to install high pressure sealed LVDTs through them. Each LVDT shall be attached to a U-Frame.

(j) Loading Device for Vertical Load for 3-D Consolidation Tests

Figure 9E:
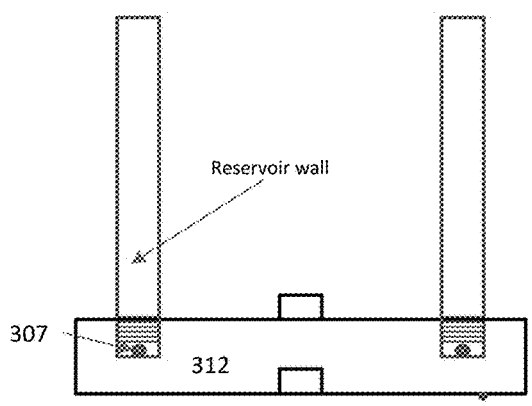
FIG. 9E shows a typical detail of open reservoir.
Figure 9F:
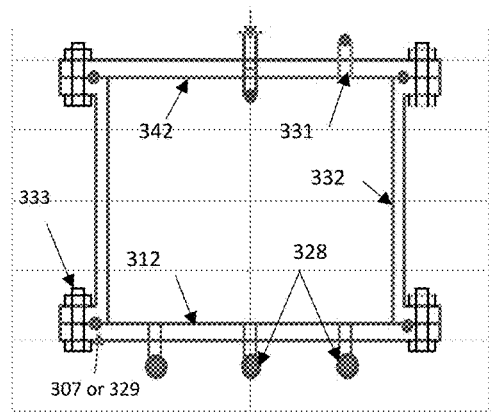
FIG. 9F shows a typical detail of a sealed reservoir.

Incremental consolidation load frame and the test procedure shall be the same as described in ASTM D-2435 and AASHTO T-216 or in the standards of national organizations of various countries. Incremental loading system and triaxial type loading system can be used for 3-D consolidation tests both for the open reservoir and for the triaxial type chamber sealed reservoir. Some designs of open reservoir system are shown in FIG. 9C, FIG. 9D and FIG. 9E, in which cylindrical is fastened to base plate 312 by screws 319 or bolts 333. These and some other designs of open reservoirs as available in the industry can also be used in 3-D consolidation tests. The triaxial type chamber and control panel has the advantage of applying the lateral fluid pressure approximately equal to the in-situ horizontal stress from where the sample was extracted to represent in-situ conditions and of saturating the specimen to 100% by back pressure saturation. Because height of the specimen for 3-D consolidation tests is between about ½" (12.7 mm) and half to three-quarter of the diameter of the soil specimen, the height of chamber to be used for 3-D consolidation test shall be about half or less than half of the height of the triaxial chamber. Using triaxial axial loading system, either (a) the load can be applied in the increments and held constant for 24 hours or (b) the strain controlled load test can also be performed, applying load to produce a selected vertical displacement at the beginning of each incremental load. The size of incremental loading system may need to be larger because of clamping rods used for triaxial type chamber/sealed reservoir. FIG. 9F shows a detail of sealed reservoir, in which the base plate 309 and top plate 342 are bolted to the cylindrical wall 342 by bolts 333 and sealed by O-rings 307 or gaskets 329. Other designs of sealed reservoirs as available in the industry can also be used for 3-D consolidation tests. Valves 328 and vent 331 like those used in the triaxial chamber are also provided. FIG. 14A show triaxial type chamber with control panel and triaxial type axial loading system, while FIG. 14B shows triaxial type chamber and control panel with incremental type loading system.

In these tests, when vertical load is increased, the horizontal resistance exerted on the specimen increases as a product of lateral strain in bands/membrane/filter fabric and its combined modulus of elasticity. In triaxial compression and 3-D consolidation tests, it is important that horizontal stresses increased by vertical stress applied on the specimen be approximately equal to those predicted by the theory of elasticity either for strip load or for circular load.

(k) Calibration Device for Expandable Jacket 301 and Flexible Ring

Figure 15:
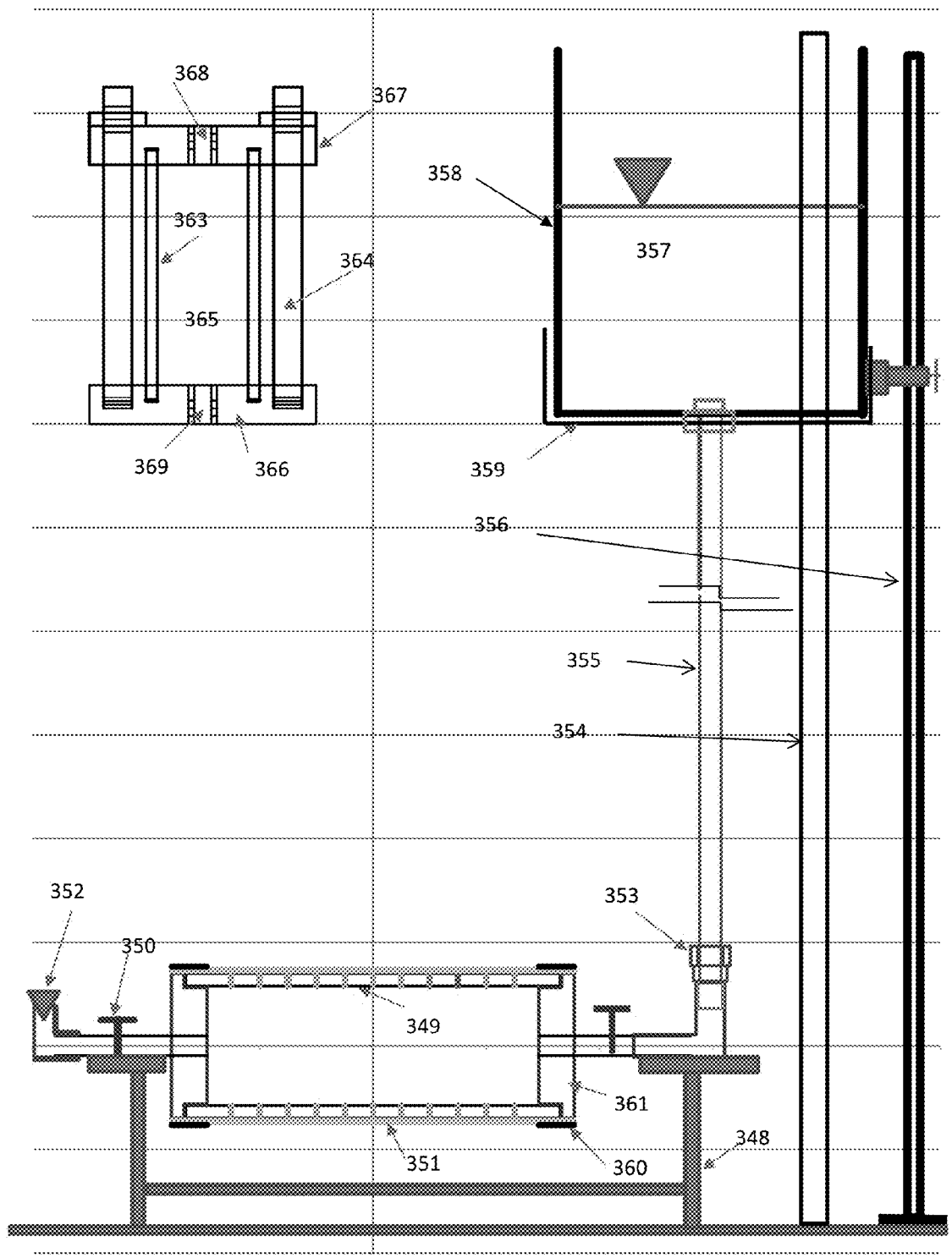
FIG. 15 shows the calibration device for determining the modulus of elasticity of elastic membrane.
Figure 16:
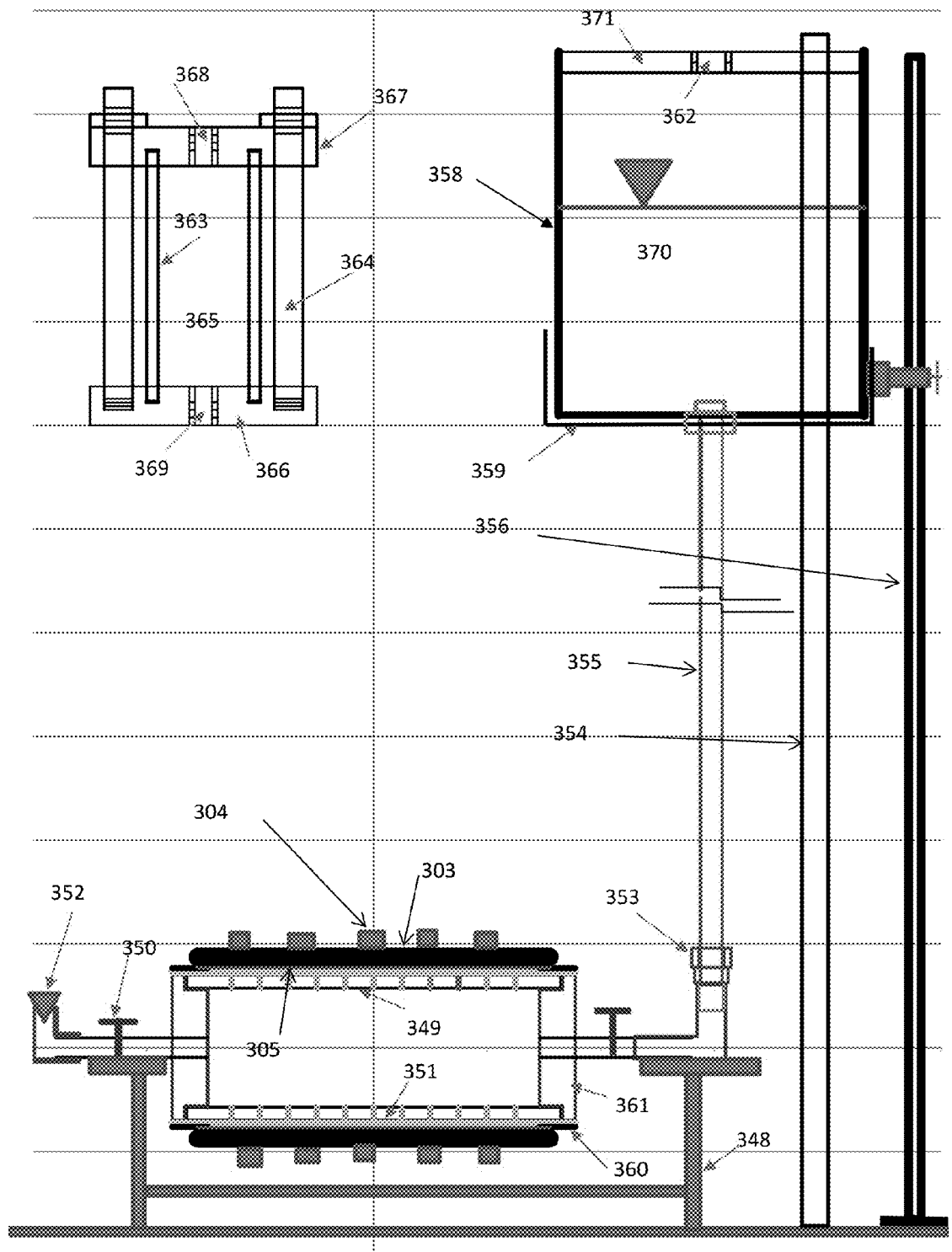
FIG. 16 shows that the calibration device for determining the combined modulus of elasticity of elastic of the expandable jacket 301 or flexible ring 302.

The calibration device as shown in in FIG. 15 and FIG. 16, consists of relatively rigid porous tube 349 with end caps 361. A stretchable and impervious membrane 351 is mounted on the porous tube 349. The membrane 351 is clamped to end caps 361. On one end, a tube with a valve 350 and a removable plug 352 shall outlet from the end caps to remove the air bubbles from water when water is filled in the porous tube 349. On the other end, another tube with a valve 350 shall outlet from the other end cap 361 and shall be connected to a flexible tube 355 using tube fitting 353 (preferably compression tube fittings) to lead towards the water reservoir 357. The reservoir shall have transparent wall 358 or 363 or 370 (preferably cylindrical wall) be supported on a movable bracket 359 which shall be clamped to a pole 356. When the clamp is loosened, the reservoir on the movable bracket 359 can be raised or lowered and clamped at the new height again. Each time, the height of water level in the reservoir over the bottom of the reservoir and over the centerline of the porous tube shall be measured by a scale mounted on the wall or on a separate stand 354. A separate vertical scale on the transparent wall 358 shall also be installed to measure height of water in the reservoir. The reservoir can be raised to any height (preferably in very small to small height increments) up to the headroom of the laboratory. Thinner membranes can be mounted on each other to make up the required overall thickness of membrane as required for the calibration test. The modulus of elasticity of the membrane 351 surrounding the porous tube 349 shall be determined. Each time before raising the reservoir 370 or 357, valve shall be closed, then reservoir raised to a predetermined height after which valve is opened, and then (i) the fall in the water level in the reservoir over its bottom is measured to calculate the volume of water expanding the membrane 351 and to calculate the radial expansion of the membrane and (ii) height of water level in reservoir over the centerline of the porous tube 349 is measured to determine the head of water or water pressure acting on the membrane 351. The data is recorded in a table and pressure versus radial displacement/radial strain is used to calculate modulus of elasticity.

The water reservoir 357 is open to atmosphere. The water reservoir 370 has a top plate 371 attached to the reservoir wall and which has a threaded hole 362, and when it is not connected to a tube connection and open, it acts as an open reservoir, open to atmosphere. But when the threaded hole 362 is provided with appropriate connections leading to a pressure chamber, air compressor or a hydraulic jack, it acts as a sealed reservoir, designed for low pressures up to 15 psi (103 kPa). In this case, water reservoir 357 need not be raised using the movable bracket. The sealed reservoir 365 shown in FIG. 15 and FIG. 16 is designed for higher pressures up to say 50 psi (345 kPa) or greater. The sealed reservoir 365 has transparent cylindrical wall 363 is provided with gasket or O-ring below and above cylindrical wall 363 and which is made water tight between bottom plate 366 and top plate 367 by use of anchor rods 364. The bottom plate 366 has a threaded hole 369 for connections leading to the porous tube 349. The top plate 367 has a threaded hole 368 for connections leading to the pressure chamber, or air compressor or a hydraulic jack or a nitrogen cylinder. The calibration device is placed on a table 348. For calibration, the pressure can be applied preferably in appropriate pressure increments, each time measuring the pressure applied, and drop in water level in the reservoir and expansion of the membrane 351 by a caliper, for using this data to calculate pressure versus radial displacement and radial strain curve, thereby to calculate modulus of elasticity of the membrane e 351. Higher pressures shall be needed for thicker expandable and impervious membranes such as high density-density polyethylene membranes (HDPE) when used in 3-D consolidation test device. Pressuremeters also use HDPE membranes, which can be calibrated in the calibration device.

To determine combined modulus of elasticity of flexible ring 302 or expandable jacket 301 including the membrane 305 (to be used in the tests) with or without filter, the additional membrane 351 surrounding the porous tube 349 is installed with or without filter 306, after which the expandable jacket 301 or flexible ring 302 consisting of segmented plates 303 and bands or rings 304 is installed. The tests are performed generally at the same levels of reservoir water levels or water pressures as done for calibration of the membrane 351 as explained above. When the readings of the previous test on the membrane 351 are deducted from the readings of the new test with expandable jacket 301 or flexible ring 302, the combined modulus of elasticity of the membrane 305 with or without filter 306, segmented plates 303 and bands or rings 304 is determined. The calibration device can also be used to determine the modulus of elasticity of any membrane, simply installing that membrane on the membrane 351 or directly on the porous tube 349 and performing the calibration test. When calibration has been previously done, then for the same expandable jacket or flexible ring, a new calibration using the calibration device may not be done or is not necessary. When the value of the modulus of elasticity of the membrane, bands or rings or the stretchable filter or combined modulus of elasticity of the flexible ring or expandable jacket is available, then calibration may not be necessary to be done.

(l) Teachings of this Application

The various aspects of what is described in the above sections, can be used alone or in other combinations for other type of tests. Teachings of this application for expandable jacket and flexible ring can be used for tests on specimen with cross-section of any round shape (such as elliptical cross-section) or with square or rectangular cross-section and different heights. Teaching of this application is applicable to other tests other than those described above, where expansion of specimen takes place for any other reasons, for example such as due to application of increment of horizontal fluid pressure inside a specimen when the specimen has a cavity or opening inside it. The teaching of this application is not limited to the tests, but it has other uses where expansion of the specimen or an object of various shapes described in the second paragraph of this section is taking place for any other activity in any real situation. Therefore, teaching of the present application has numerous advantages and uses. It should be noted that the teaching of this application is not limited to the tests described in this application. It should therefore be noted that this is not an exhaustive list and there may be other advantages and uses which are not described herein.

Although the teaching of the present application and claims has been described in detail for purpose of illustration, it is understood that such detail is solely for that purpose, and variations can be made therein by those skilled in the art without departing from the scope of the teaching of this application. For example, filter disk below and above the specimen placed primarily for preventing clogging by fine particles in porous discs, may be deleted to avoid its influence on the compressibility of the specimen and instead porous disks regularly cleaned by ultrasonic or boiling and brushing may be done. Similarly, if for certain soils, the membrane surrounding the porous disk remains in tight contact with no separation during the tests, then the additional band or removable adhesive stretchable tape need not be provided surrounding the membrane and O-ring. Features described in the preceding description/specification may be used in combination other than the combinations explicitly described. Whilst endeavoring in the forgoing specification/description to draw attention to those features of the invention believed to be of particular importance, it should be understood that Applicant and Inventor claims protection in respect of any patentable feature or combinations of features hereinbefore referred to and/or shown in the drawings/figures whether or not particular emphasis has been placed thereon.

The term "comprising" as used in the claims does not exclude other elements or steps. The term "a" or "an" as used in the claims does not exclude plurality. A unit or other means may fulfill the functions of several units or means recited in the claims.

(m) References

ASTM Standards (2007), Standard Test Methods for Unconsolidated-Undrained Triaxial Compression Tests on Cohesive Soils. ASTM D2850-03, *American Society for Testing and Materials*, Philadelphia, Pa.

ASTM Standards (2011), Standard Test Methods for Consolidated-Undrained Triaxial Compression Tests on Cohesive Soils. ASTM D4767-11, *American Society for Testing and Materials*, Philadelphia, Pa.

AASHTO (2012), Standard Method of Test for One-Dimensional Consolidation Properties of Soils, *American Association of State Highway and Transportation Officials*, Washington, D.C.

ASTM Standards (2011), Standard Test Method for Determining One-Dimensional Consolidation Properties of Soils, ASTM D2435/D2435 M, *American Society for Testing and Materials*, Philadelphia, Pa.

ASTM Standards (2011) Standard Test Method for Compressive Strength and Elastic Moduli of Rocks. ASTM: D 7012. *American Society for Testing and Materials*, Philadelphia, Pa.

Bishop, A. W. and Green, G. E. (1965). "The influence of end restraint on the compression strength of a cohesionless soil," Geotechnique, Vol. 15, pp. 243-266.

Fang, H (1990), Foundation Engineering Handbook, $2^{nd}$ Edition, *Van Nostrand Reinhold*, New York.

Gupta, R. C. (2016). "Expandable jacket 301 and Its Calibration Device for Triaxial Tests on Soils," U.S. Pat. No. 9,383,346 B2, United States Patent and Trademark Office, Alexandria, Va. 22313.

Gupta, R. C. (2016). "Test Device for Determining Three-dimensional Consolidation Properties of Soils," U.S. Pat. No. 9,567,722 B2, United States Patent and Trademark Office, Alexandria, Va. 22313.

Gupta, R. C. (2016). "Test Device for Determining Three-dimensional Consolidation Properties of Soils," U.S. Pat. No. 9,546,940 B2, United States Patent and Trademark Office, Alexandria, Va. 22313.

Gupta, R. C. (2016). "Expandable jacket 301 and Its Calibration Device for Triaxial Tests on Soils," Publication No. WO 2016/14918, The International Bureau of WIPO, Geneva-20, Switzerland.

Gupta, R. C. (2016). "Test Device for Determining Three-dimensional Consolidation Properties of Soils," Publication No. WO 2016/196731, The International Bureau of WIPO, Geneva-20, Switzerland.

Lee, K. L. (1978). "End restraint effects on undrained static triaxial strength of sand," *Journal of Geotechnical Engineering Division*, Vol. 104, pp. 687-703.

Perloff, W. H., and Baron, W. (1976), SOIL MECHANICS, John Wiley and Sons, New York.

Rochelle, P. L., Leroueil, S., Trak, B., Blais-Lerox, L., and Tavenas, F. (1988). "Observational approach to membrane and area corrections in triaxial tests," Advanced Triaxial Testing of Soil and Rock, ASTM, STP 977, Eds. R. T. Donaghe, Chaney, R. C., Silver, M. L., ASTM, Philadelphia, pp. 715-731.

Rowe, P. W. and Barden, L. (1964). "Importance of free ends in triaxial testing," Journal of *Soil Mechanics and Foundations Division*, ASCE, Vol. 90, No. SM1, pp. 1-27.

Skempton, A. W., and Bjerrum, L. (1957), A Contribution to the Settlement Analyses of Foundations on Clay, *Geotechnique* 7, No. 3

Winterkorn H. F., and Fang, H. (1975), Foundation Engineering Handbook, *Van Nostrand Reinhold Company*, New York.

The invention claimed is:

1. An expandable jacket for maintaining uniform radial expansion of a specimen, required for determining accurately the area of cross-section, volume change characteristics, deviator stress, shear strength, modulus of elasticity and Poisson's ratio, during triaxial compression tests on soils and intermediate geomaterials, and during unconfined compressive strength tests on cohesive soils, and cohesive intermediate geomaterials and soft rocks, the expandable jacket comprising:
   (i) a filter disc placed on a first porous disk to receive a specimen, said porous disk resting on the rigid specimen base plate; wherein a second filter disc placed on the top of the specimen; wherein a second porous disk placed on top of the second filter disk; wherein a rigid specimen cap of the triaxial chamber placed on top of the second porous disk wherein at least a stretchable and impervious membrane placed such that the membrane surrounds and is in contact with the specimen, and extends to the porous disks and to the specimen base plate and cap;
   (ii) stretchable O-rings installed to seal the membrane to the specimen cap and base; wherein in addition a stretchable band or ring or removable adhesive tape of sufficient width is installed surrounding the first porous disk and O-ring and surrounding the second porous disk and O-ring, when considered necessary to take additional precaution to maintain tight contact of the membrane to the disks;
   (iii) a plurality of segmented plates assembled vertically such that the assembled segmented plates surround and are in contact with the membrane; wherein each of the segmented plates extend vertically beyond or up to the first porous disk and the second porous disk; wherein the segmented circular shaped plates are sufficiently thick not to bend and remain vertical, with the flexible lateral support provided by the stretchable bands or rings during the tests;
   (iv) at least one band or ring which stretch to permit radial expansion of the specimen, placed such that each of the band or ring surround and are in contact with each of the segmented plates;
   (v) the test is performed with or without measurement of the radial displacement/expansion of the specimen.

2. The flexible ring with a triaxial type loading system or a conventional incremental loading system, and either a triaxial type chamber/sealed reservoir and a triaxial type control panel or an open reservoir, for performing three-dimensional consolidation test to determine three-dimensional coefficient of consolidation of soils and intermediate geomaterials, the flexible ring comprising:
   (i) a filter disk placed on a first porous disk to receive a specimen, said porous disk resting on the rigid specimen base plate; wherein a second filter disk placed on the top of the specimen; wherein a second porous disk placed on top of the second filter disk; wherein a rigid specimen cap placed on top of the second porous disk; wherein a filter placed such that the filter surrounds and is in contact with the specimen and porous disks;
   (ii) at least a stretchable and impervious membrane placed such that the membrane surrounds and is in contact with the filter; wherein for triaxial type chamber/sealed reservoir, the membrane extends beyond the filter and extends to the porous disks and the specimen base plate and cap; wherein for the open reservoir, the filter extends beyond the membrane and both the filter and membrane extends to the base plate and cap;
   (iii) stretchable O-rings installed to seal the membrane to the specimen cap and base; wherein in addition a stretchable band or ring or removable adhesive tape of sufficient width is installed surrounding the first porous disk and O-ring and surrounding the second porous disk and O-ring, when considered necessary to take additional precaution to maintain tight contact of the membrane to the disks;
   (iv) a plurality of segmented plates assembled vertically such that the assembled segmented plates surround and are in contact with the membrane; wherein each of the segmented plates extend vertically beyond or up to the first porous disk and the second porous disk; wherein the segmented circular shaped plates are sufficiently thick not to bend and remain vertical, with the flexible lateral support provided by the stretchable bands or rings during the tests;
   (v) at least one band or ring, which stretch to permit the radial expansion of the specimen while applying lateral pressure on the specimen, placed such that each of the band or ring surround and are in contact with each of the segmented plates;
   (vi) the test is performed with or without measurement of radial displacement of the specimen.

3. The flexible ring with a triaxial type loading system or a conventional incremental loading system, and either the triaxial type chamber/sealed reservoir and the triaxial type control panel or the open reservoir, for performing three-dimensional consolidation test to determine coefficient of consolidation in vertical direction of soils and intermediate geomaterials and to determine three-dimensional settlement characteristics of soils and intermediate geomaterials, the flexible ring comprising:
   (i) a filter disk placed on a first porous disk to receive a specimen, said porous disk resting on the rigid specimen base plate; wherein a second filter disk placed on the top of the specimen; wherein a second porous disk placed on top of the second filter disk; wherein a rigid specimen cap placed on top of the second porous disk;
   (ii) at least a stretchable and impervious membrane placed such that the membrane surrounds and is in contact with the cylindrical specimen; wherein the membrane extends to the porous disks and the specimen base plate and cap;
   (iii) stretchable O-rings installed to seal the membrane to the specimen cap and base; wherein in addition, a stretchable band or ring or removable adhesive tape of sufficient width is installed surrounding the first porous disk and O-ring and surrounding the second porous disk and O-ring, when considered necessary to take additional precaution to maintain tight contact of the membrane to the disks;
   (iv) a plurality of segmented plates assembled vertically such that the assembled segmented plates surround and are in contact with the membrane; wherein each of the segmented plates extend vertically beyond or up to the first porous disk and the second porous disk; wherein the segmented circular shaped plates are sufficiently thick not to bend and remain vertical, with the flexible lateral support provided by the stretchable bands or rings during the tests;

(v) at least one band or ring, which stretch to permit radial expansion of the specimen while applying lateral pressure on the specimen, placed such that each of the band or ring surround and are in contact with each of the segmented plates;

(vi) the test is performed with or without measurement of radial displacement/expansion of the specimen.

4. The flexible ring with a triaxial type loading system or a conventional incremental loading system, and either a triaxial type chamber/sealed reservoir and a triaxial type control panel or and the open reservoir, for performing three-dimensional consolidation test to determine coefficient of consolidation of soils and intermediate geomaterials in horizontal direction, the flexible ring comprising:

(i) for open reservoir, a rigid specimen cap and rigid base not containing drainage ports are placed below the specimen and top of the specimen, respectively; wherein for triaxial chamber/sealed reservoir a rigid plate not containing drainage ports placed between the specimen and the rigid specimen base containing drainage ports; wherein a rigid plate not containing drainage ports placed between the specimen and the rigid specimen cap containing drainage ports; wherein a filter placed such that the filter surrounds and is in contact with the specimen; and wherein the filter extends around the rigid base and rigid specimen cap;

(ii) at least a stretchable and impervious membrane placed such that the membrane surrounds and is in contact with the filter; wherein for triaxial type chamber/sealed reservoir, the membrane extends beyond the filter and extends to the specimen base plate and cap; wherein for the open reservoir, the filter extends beyond the membrane and both the filter and membrane extend to the base plate and cap;

(iii) stretchable O-rings installed to seal the membrane to the specimen cap and base; wherein in addition, a stretchable band or ring or removable adhesive tape of sufficient width is installed surrounding the first porous disk and O-ring and surrounding the second porous disk and O-ring, when considered necessary to take additional precaution to maintain tight contact of the membrane to the disks;

(iv) a plurality of segmented plates assembled vertically such that the assembled segmented plates surround and are in contact with the membrane; wherein each of the segmented plates extend vertically beyond or up to the first porous disk and the second porous disk; wherein the segmented circular shaped plates are sufficiently thick not to bend and remain vertical, with the flexible lateral support provided by the stretchable bands or rings during the tests;

(v) at least one band or ring, which stretch and permit the radial expansion of the specimen while applying lateral pressure on the specimen, placed such that each of the band or ring surround and are in contact with each of the segmented plates;

(vi) the test is performed with or without measurement of radial displacement of the specimen.

5. An expandable jacket according to claim 1 for measurement of the radial displacement by LVDT or strain gages, the expandable jacket further comprises:

(i) wherein for measurement of the radial displacement, at least one LVDT which is capable to resist the high fluid pressure without any damage or malfunctioning of the electronics of LVDT, its connector, and its cable exit from the connector and its cable; wherein LVDT is removably attached to a spring-leaded U-frame; wherein LVDT with either radial connector or axial connector is used; wherein a specially designed sealed exit either for the sealed cable or for the rear end of the connector is provided from either top plate or cylindrical wall of the chamber;

(ii) wherein for measurement of the radial displacement by strain gages, strain gages specially designed with adequate precaution taken to protect the electronics of strain gages and their cable against fluid pressures in the pressure chamber; wherein a specially designed sealed exit provided from either top plate of the chamber or from the cylindrical wall of the chamber; wherein strain gages removably attached to the spring loaded U-frame;

(iii) wherein during measurement of radial displacement, the spring-loaded U-frame rests on ball bearings such that during radial expansion of the specimen, the spring-loaded U-frame maintains the LVDT in proper horizontal alignment and prevents the LVDT from being inclined due to the vertical settlement of the specimen.

6. The flexible ring according to claim 2 for measurement of the radial displacement by LVDT or strain gages, the flexible ring further comprises:

(i) wherein for measurement of the radial displacement, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable or for the rear end of the connector is provided from either top plate or cylindrical wan of the chamber/sealed reservoir;

(ii) wherein for measurement of the radial displacement in the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;

(iii) wherein for measurement of the radial displacement by strain gages, strain gages specially designed with adequate precaution taken to protect the electronics of strain gages and their cable against fluid pressures in the pressure chamber or from water in open reservoir; wherein a specially designed sealed exit provided from either top plate of the chamber or from the cylindrical wall of the chamber or open reservoir wherein exit provided for the strain gage or its cable from water level in open reservoir with adequate precautions; wherein strain gages removably attached to the spring loaded U-frame;

(iv) wherein during measurement of radial displacement, the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical.

7. The flexible ring according to claim 3 for measurement of the radial displacement by LVDT or strain gages, the flexible ring further comprises:
   (i) wherein for measurement of the radial displacement, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit either for the sealed cable or for the rear end of the connector is provided from either top plate or cylindrical wall of the chamber/sealed reservoir;
   (ii) wherein for measurement of the radial displacement in the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;
   (iii) wherein for measurement of the radial displacement by strain gages, strain gages specially designed with adequate precaution taken to protect the electronics of strain gages and their cable against fluid pressures in the pressure chamber or from water in open reservoir; wherein a specially designed sealed exit provided from either top plate of the chamber or from the cylindrical wall of the chamber or open reservoir; wherein exit provided for the strain gage or its cable from water level in open reservoir with adequate precautions; wherein strain gages removably attached to the spring loaded U-frame;
   (iv) wherein during measurement of radial displacement, the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical.

8. The flexible ring according to claim 4 for measurement of the radial displacement by LVDT or strain gages, the flexible ring further comprises:
   (i) wherein for measurement of the radial displacement, at least one LVDT which is capable to resist the high fluid pressure without any damage or malfunctioning of the electronics of LVDT, its connector, and its cable exit from the connector and its cable; wherein LVDT is removably attached to a spring-loaded U-frame; wherein LVDT with either radial connector or axial connector is used; wherein a specially designed sealed exit ether for the sealed cable or for the rear end of the connector is provided from either top plate or cylindrical wall of the chamber/sealed reservoir;
   (ii) wherein measurement of the radial displacement in the open reservoir, at least one LVDT capable to resist the water in the open reservoir and moisture without any damage or malfunctioning of electronics of LVDT, its connector and its cable; wherein LVDT is removably attached to a spring-loaded U-frame; wherein LVDT with either radial or axial connector is used; wherein LVDT with radial connector and/or its cable exits from top of the water level; wherein the sealed exit to the LVDT with axial connector is provided from the cylindrical wall of the open reservoir;
   (iii) wherein for measurement of the radial displacement by strain gages, strain gages specially designed with adequate precaution taken to protect the electronics of strain gages and their cable against fluid pressures in the pressure chamber or from water in open reservoir; wherein a specially designed sealed exit provided from either top plate of the chamber or from the cylindrical wall of the chamber or open reservoir; wherein edit provided for the strain gage or its cable from water level in open reservoir with adequate precautions; wherein strain gages removably attached to the spring loaded U-frame;
   (iv) wherein during measurement of radial displacement, the spring-loaded U-frame rests on ball bearings such that during radial expansion of the cylindrical specimen, the spring-loaded U-frame maintains the LVDT in proper horizontal alignment and prevents the LVDT from being inclined due to the vertical settlement of the cylindrical.

9. The expandable jacket according to claim 5, when the measurement of the radial displacement of the specimen is made by LVDT, the expandable jacket further comprises:
   (i) wherein for measurement of the radial displacement of the specimen in triaxial chamber/sealed reservoir, a high pressure sealed (i.e. hermetically sealed) LVDT with the radial connector sealed to the LVDT body, and sealed/shielded cable with the sealed exit from the connector capable to resist the high fluid pressure without any damage or malfunctioning of the LVDT and its electronics is used; wherein a specially designed sealed exit for the sealed cable of the radial connector is provided through the top metal plate of the chamber/sealed reservoir with at least one O-ring between sealed cable and a metal plug threaded on the other side and either at least one O-ring between the threaded opening and its threaded metal plug or threaded metal plug wounded by the PTFE with or without O-ring around the threaded opening and its threaded metal plug;
   (ii) wherein for measurement of the radial displacement of the specimen in the triaxial chamber/sealed reservoir, the high pressure sealed LVDT with the axial connector sealed to the LVDT body and with a threaded length at the rear end of the LVDT body is used; wherein a specially designed sealed exit is provided for the rear end of the LVDT body through the metal cylindrical wall, using an internally threaded metal tube weld connected to the metal cylindrical wall; wherein the threaded length of the LVDT body is fastened to the threaded metal tube and sealed with O-rings.

10. The flexible ring according to claim 6, when the measurement of the radial displacement of the specimen is made by LVDT, the flexible ring further comprises:
   (i) wherein for measurement of the radial displacement of the specimen in triaxial chamber/sealed reservoir, a high pressure sealed (i.e. hermetically sealed) LVDT with the radial connector sealed to the LVDT body, and sealed/shielded cable with the sealed exit from the connector capable to resist the high fluid pressure without any damage or malfunctioning of the LVDT and its electronics is used; wherein a specially designed sealed exit for the sealed cable of the radial connector is provided through the top metal plate of the chamber/sealed reservoir with at least one O-ring between sealed cable and a metal plug threaded on the other side and either at least one O-ring between the threaded opening and its threaded metal plug or threaded metal plug wounded by the PTFE with or without O-ring around the threaded opening and its threaded metal plug;

(ii) wherein for measurement of the radial displacement of the specimen in the triaxial chamber/sealed reservoir or in open reservoir, the high pressure sealed LVDT with the axial connector sealed to the LVDT body and with a threaded length at the rear end of the LVDT body is used; wherein a specially designed sealed exit is provided for the rear end of the LVDT body through the metal cylindrical wall, using an internally threaded metal tube weld connected to the metal cylindrical wall; wherein the threaded length of the LVDT body is fastened to the threaded metal tube and sealed with O-rings.

11. The flexible ring according to claim 7, when the measurement of the radial displacement of the specimen is made by LVDT, the flexible ring further comprises:

(i) wherein for measurement of the radial displacement of the specimen in triaxial chamber/sealed reservoir, a high pressure sealed (i.e. hermetically sealed) LVDT with the radial connector sealed to the LVDT body, and sealed/shielded cable with the sealed exit from the connector capable to resist the high fluid pressure without any damage or malfunctioning of the LVDT and its electronics is used; wherein a specially designed sealed exit for the sealed cable of the radial connector is provided through the top metal plate of the chamber/sealed reservoir with at least one O-ring between sealed cable and a metal plug threaded on the other side and either at least one O-ring the threaded opening and its threaded metal plug or threaded metal plug wounded by the PTFE with or without O-ring around the threaded opening and its threaded metal plug;

(ii) wherein for measurement of the radial displacement of the specimen in the triaxial chamber/sealed reservoir or in open reservoir, the high pressure sealed LVDT with the axial connector sealed to the LVDT body and with a threaded length at the rear end of the LVDT body is used; wherein a specially designed sealed exit is provided for the rear end of the LVDT body through the metal cylindrical wall, using an internally threaded metal tube weld connected to the metal cylindrical wall; wherein the threaded length of the LVDT body is fastened to the threaded metal tube and sealed with O-rings.

12. The flexible ring according to claim 8, when the measurement of the radial displacement of the specimen is made by LVDT, the flexible ring further comprises:

(i) wherein for measurement of the radial displacement of the specimen in triaxial chamber/sealed reservoir, a high pressure sealed (i.e. hermetically sealed) LVDT with the radial connector sealed to the LVDT body, and sealed/shielded cable with the sealed exit from the connector capable to resist the high fluid pressure without any damage or malfunctioning of the LVDT and its electronics is used; wherein a specially designed sealed exit for the sealed cable of the radial connector is provided through the top metal plate of the chamber/sealed reservoir with at least one O-ring between sealed cable and a metal plug threaded on the other side and either at least one O-ring between the threaded opening and its threaded metal plug or threaded metal plug wounded by the PTFE with or without O-ring around the threaded opening and its threaded metal plug;

(ii) wherein for measurement of the radial displacement of the specimen in the triaxial chamber/sealed reservoir or in open reservoir, the high pressure sealed LVDT with the axial connector sealed to the LVDT body and with a threaded length at the rear end of the LVDT body is used; wherein a specially designed sealed exit is provided for the rear end of the LVDT body through the metal cylindrical wall, using an internally threaded metal tube weld connected to the metal cylindrical wall; wherein the threaded length of the LVDT body is fastened to the threaded metal tube and sealed with O-rings.

13. An expandable jacket according to claim 1, the expandable jacket further comprises:

(i) wherein each of the segmented plates either does not contain screw mounts or contains at least one screw mount or unthreaded holes located at least at one predetermined height of each of the segmented plates;

(ii) wherein the expandable jacket comprising the segmented circular shaped plates and bands or rings are installed around the membrane containing specimen by use of the removable attachments;

(iii) wherein removable attachments comprising: two horizontal separate half-circular brackets, or at least one horizontal hook and loop strap or brackets and horizontal hook and loop straps both in combination for vertical positioning of each of the segmented plate; wherein the circular shaped segmented plates are either vertically assembled and screwed to screw mounts in brackets and segmented plates or through holes in hook and loop straps and screw mounts in the segmented plates at least one predetermined height or by snap on pins in unthreaded holes at least at one predetermined height or vertically assembled using removable adhesive hook and loop straps in contact with the segmented plates at least at one predetermined height; wherein at least one band or ring placed such that each of the bands or rings surround and are in contact with each of the segmented plates; wherein after assembling the segmented plates and bands or rings properly, the removable attachments of brackets or straps are removed;

(iv) wherein the expandable jacket is calibrated using a calibration device to determine the modulus of elasticity of the membrane and combined modulus of elasticity of the membrane and the expandable jacket; and wherein when the modulus of elasticity of the membrane, bands and rings or combined modulus of elasticity of the membrane and the expandable jacket is known then the calibration may not be necessary to be done;

(v) wherein the calibration device comprising: a water reservoir, wherein the water reservoir has a vertical position defined by a vertically movable bracket for increasing height over centerline of the porous tube in appropriate height increments; or wherein the water reservoir in a pressure chamber for applying fluid pressure in appropriate increments; wherein a horizontal porous tube with end caps connected to the vertically movable water reservoir or to the water reservoir in the pressure chamber via at least one tube and valve, wherein on the other end, another tube exits the porous tube with a valve to initially flush out air bubbles from water; wherein the porous tube is configured to be surrounded and sealed by the membrane; wherein the horizontal porous tube which is surrounded by the membrane is further configured to be surrounded by an additional membrane with or without the filter and flexible ring or expandable jacket consisting of the segmented plates, and at least one band or ring.

14. The flexible ring according to claim 2, the flexible ring further comprises:
   (i) wherein each of the segmented plates either do not contain screw mounts or contains at least one screw mount or unthreaded holes located at least at one predetermined height of each of the segmented plates;
   (ii) wherein the flexible ring comprising the segmented circular shaped plates and bands or rings are installed around the membrane containing the filter and the specimen by use of the removable attachments;
   (iii) wherein the removable attachments comprising horizontal separate half-circular brackets, or at least one horizontal hook and loop strap or brackets and horizontal hook and loop straps both in combination for vertical positioning of each of the segmented plate; wherein the circular shaped segmented plates are either vertically assembled and screwed to screw mounts in brackets and segmented plates or through holes in hook and loop straps and screw mounts in the segmented plates at least one redetermined height or by snap on pins in unthreaded holes at least at one predetermined height or vertically assembled using removable adhesive hook and loop straps in contact with the segmented plates at least at one predetermined height wherein at least one band or ring placed such that each of the bands or rings surround and are in contact with each of the segmented plates; wherein after assembling the segmented plates and bands or rings properly, the removable attachments of brackets or straps are removed;
   (iv) wherein the flexible ring is calibrated using the calibration device to determine the modulus of elasticity of the membrane and combined modulus of elasticity of the membrane, the filter and the flexible ring; and wherein when combined modulus of elasticity of the membrane, the filter and the flexible ring is known then the calibration may not be necessary;
   (v) wherein the calibration device comprising: a water reservoir; wherein the water reservoir has a vertical position defined by a vertically movable bracket for increasing height over centerline of the porous tube in appropriate height increments; or wherein the water reservoir in a pressure chamber for applying fluid pressure in appropriate increments; wherein a horizontal porous tube with end caps connected to the vertically movable water reservoir or to the water reservoir in the pressure chamber via at least one tube and valve, wherein on the other end, another tube exits the porous tube with a valve to initially flush out air bubbles from water, wherein the porous tube is configured to be surrounded and sealed by the membrane; wherein the horizontal porous tube which is surrounded by the membrane is further configured to be surrounded by an additional membrane with the filter and flexible ring or expandable jacket consisting of the segmented plates, and at least one band or ring.

15. The flexible ring according to claim 3, the flexible ring further comprises:
   (i) wherein each of the segmented plates either does not contain screw mounts or contains at least one screw mount or unthreaded holes located at least at one predetermined height of each of the segmented plates;
   (ii) wherein the flexible ring comprising of segmented circular shaped plates and bands or rings are installed around the membrane containing the specimen by use of the removable attachments;
   (iii) wherein the removable attachments comprising: horizontal separate half-circular brackets, or at least one horizontal hook and loop strap or brackets and horizontal hook and loop straps both in combination for vertical positioning of each of the segmented plate; wherein the circular shaped segmented plates are either vertically assembled and screwed to screw mounts in brackets and segmented plates or through holes in hook and loop straps and screw mounts in the segmented plates at least one redetermined height or by snap on pins in unthreaded holes at least at one predetermined height or vertically assembled using removable adhesive hook and loop straps in contact with the segmented plates at least at one predetermined height; wherein at least one band or ring placed such that each of the bands or rings surround and are in contact with each of the segmented plates; wherein after assembling the segmented plates and bands or rings properly, the removable attachments of brackets or straps are removed;
   (iv) wherein the flexible ring is calibrated using the calibration device to determine the modulus of elasticity of the membrane and combined modulus of elasticity of the membrane and flexible ring; wherein when combined modulus of elasticity of the membrane and the flexible ring is known then the calibration may not be necessary;
   (v) wherein the calibration device comprising: a water reservoir, wherein the water reservoir has a vertical position defined by a vertically movable bracket for increasing height over centerline of the porous tube in appropriate height increments; or wherein the water reservoir in a pressure chamber for applying fluid pressure in appropriate increments; a horizontal porous tube with end caps connected to the vertically movable water reservoir or to the water reservoir in the pressure chamber via at least one tube and valve, wherein on the other end, another tube exits the porous tube with a valve to initially flush out air bubbles from water; wherein the porous tube is configured to be surrounded and sealed by the membrane; wherein the horizontal porous tube which is surrounded by the membrane is further configured to be surrounded by an additional membrane with the filter and flexible ring or expandable jacket consisting of the segmented plates, and at least one band or ring.

16. The flexible ring according to claim 4, the flexible ring further comprises:
   (i) wherein each of the segmented plates either does not contain screw mounts or contains at least one screw mount or unthreaded holes located at least at one predetermined height of each of the segmented plates;
   (ii) wherein the flexible ring comprising the segmented circular shaped plates and bands or rings are installed around the membrane containing the filter and the specimen by use of the removable attachments;
   (iii) wherein the removable attachments comprising: horizontal separate half-circular brackets, or at least one horizontal hook and loop strap or brackets and horizontal hook and loop straps both in combination for vertical positioning of each of the segmented plate; wherein the circular shaped segmented plates are either vertically assembled and screwed to screw mounts in brackets and segmented plates or through holes in hook and loop straps and screw mounts in the segmented plates at least one predetermined height or by snap on pins in unthreaded holes at least at one predetermined height or vertically assembled using removable adhesive hook and loop straps in contact with the segmented plates at least at one predetermined height; wherein at least one band or ring placed such that each of the bands or rings surround and are in contact with each of the segmented plates; wherein after assembling the segmented plates and bands or rings properly, the removable attachments of brackets or straps are removed;

(iv) wherein the flexible ring is calibrated using the calibration device to determine the modulus of elasticity of the membrane and combined modulus of elasticity of the membrane, and flexible ring; wherein when combined modulus of elasticity of the membrane, the filter and the flexible ring is known then calibration may not be necessary;

(v) wherein the calibration device comprising: a water reservoir, wherein the water reservoir has a vertical position defined by a vertically movable bracket for increasing height over centerline of the porous tube in appropriate height increments; or wherein the water reservoir in a pressure chamber for applying fluid pressure in appropriate increments; wherein a horizontal porous tube with end caps connected to the vertically movable water reservoir or to the water reservoir in the pressure chamber via at least one tube and valve, wherein on the other end, another tube exits the porous tube with a valve to initially flush out air bubbles from water, wherein the porous tube is configured to be surrounded and sealed by the membrane; wherein the horizontal porous tube which is surrounded by the membrane is further configured to be surrounded by an additional membrane with or without the filter and flexible ring or expandable jacket consisting of the segmented plates, and at least one band or ring.

17. The expandable jacket or flexible ring for maintaining uniform radial expansion of a radially expanding specimen, the expandable jacket or flexible ring comprising:

(i) a plurality of segmental circular arch shaped plates assembled vertically such that the assembled segmental plates surround and are in contact with the specimen or the membrane surrounding the specimen or with the membrane surrounding the filter and the specimen; wherein segmental plates are sufficiently thick and strong not to bend and remain vertical with flexible lateral support provided by stretchable bands or rings during the tests;

(ii) At least one stretchable band or ring, which stretch to permit radial expansion of the specimen while applying lateral pressure on the specimen, installed such that each of the band or ring surround and are in contact with each of the segmental plates.

18. The expandable jacket or flexible ring according to claim 17, the LVDT or strain gage when required for measuring the radial expansion of the specimen, the expandable jacket or flexible ring further comprises:

(i) at least one LVDT of strain gage removable attached to a spring-loaded U-frame or to a non-spring-loaded U-frame;

(ii) wherein the U-frame rests on ball bearings such that during radial expansion of the specimen; wherein, the U-frame maintains the LVDT or strain gage in proper horizontal position and prevents the LVDT or strain gage from getting inclined due to the vertical settlement of the specimen;

(iii) Wherein the U-frame placed on a block resting on the bottom plate of the loading device.

* * * * *